(12) United States Patent
Liu et al.

(10) Patent No.: US 9,304,234 B2
(45) Date of Patent: Apr. 5, 2016

(54) PLASMONIC DARK FIELD AND FLUORESCENCE MICROSCOPY

(75) Inventors: Zhaowei Liu, San Diego, CA (US); Feifei Wei, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 1033 days.

(21) Appl. No.: 13/418,097

(22) Filed: Mar. 12, 2012

(65) Prior Publication Data

US 2012/0229891 A1 Sep. 13, 2012

Related U.S. Application Data

(60) Provisional application No. 61/451,504, filed on Mar. 10, 2011.

(51) Int. Cl.
  *G02B 5/00* (2006.01)
  *G01N 21/552* (2014.01)
  *G01N 21/64* (2006.01)

(52) U.S. Cl.
  CPC ............ *G02B 5/008* (2013.01); *G01N 21/553* (2013.01); *G01N 21/648* (2013.01); *G01N 21/6458* (2013.01); *G01N 2201/062* (2013.01); *G01N 2201/0628* (2013.01)

(58) Field of Classification Search
  CPC ............................. G02B 6/1226; G02B 13/14
  See application file for complete search history.

(56) References Cited

U.S. PATENT DOCUMENTS 7,265,845 B2 * 9/2007 Kochergin .................. 356/445
2006/0127946 A1 * 6/2006 Montagu et al. ............. 435/7.1

OTHER PUBLICATIONS

Hu, H. et al. (2010, e-published Mar. 18, 2010). "Plasmonic Dark Field Microscopy," *Applied Physics Letters* 96:113107, 3 pages.

* cited by examiner

*Primary Examiner* — David Porta
*Assistant Examiner* — Faye Boosalis
(74) *Attorney, Agent, or Firm* — Mintz Levin Cohn Ferris Glovsky and Popeo, P.C.

(57) ABSTRACT

Plasmonic condensers for generating surface plasmon at an evanescent wave surface can include a substrate layer, a metal layer comprising the evanescent wave surface; and a media layer disposed between the metal layer and the substrate layer. The media layer can be active or passive and can include a source of radiation that interacts with the metal layer to create surface plasmons that are not substantially optically detectable as far field radiation until an interfering object is brought into proximity with the evanescent wave surface. When an interfering object such as a sample or specimen is brought into proximity with the evanescent wave surface, it causes coupling of at least some of the surface plasmons into propagating radiation detectable by an objective lens. Systems, methods, and the like are disclosed, as are features of a plasmonic meta-materials illuminator.

18 Claims, 25 Drawing Sheets

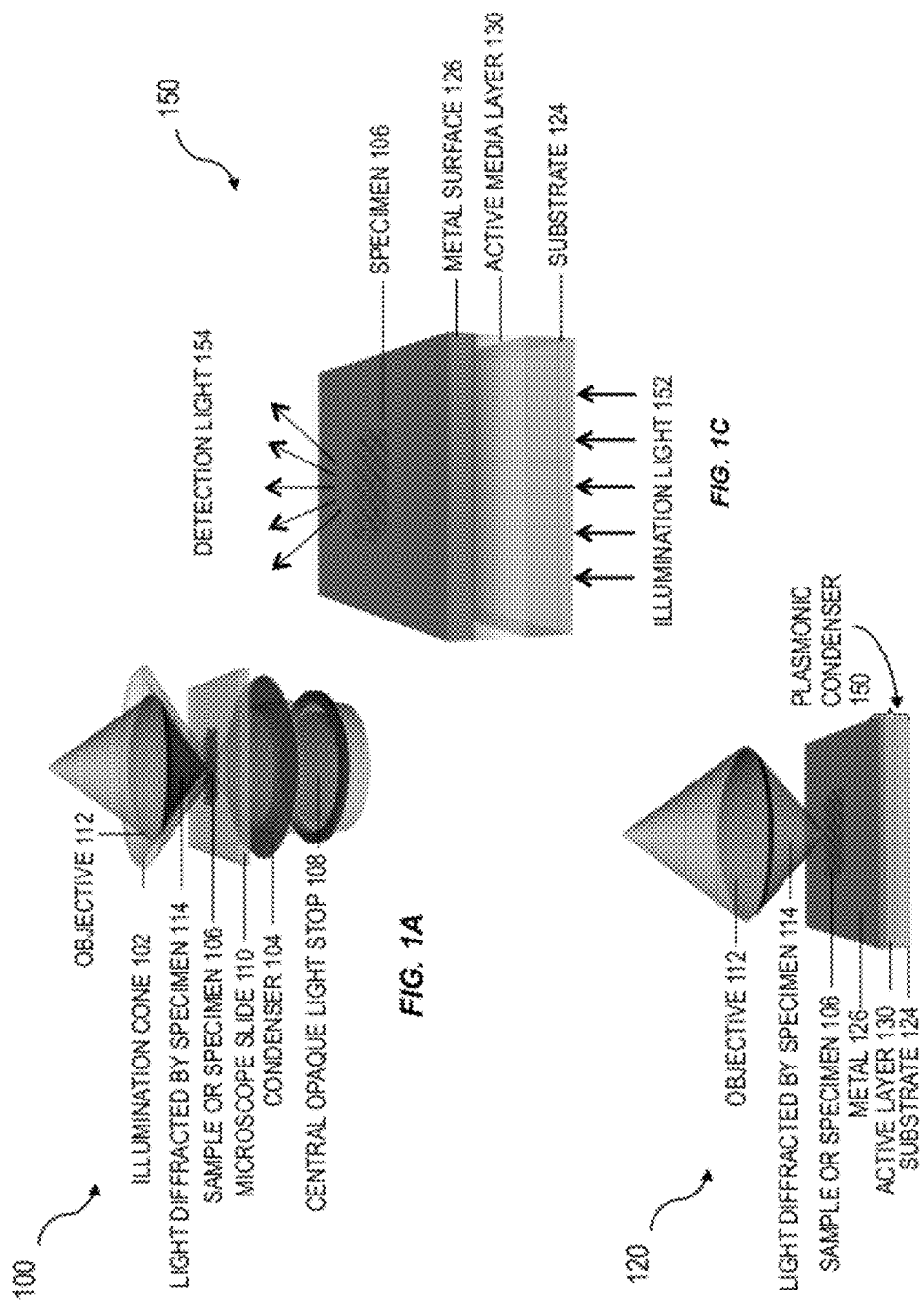

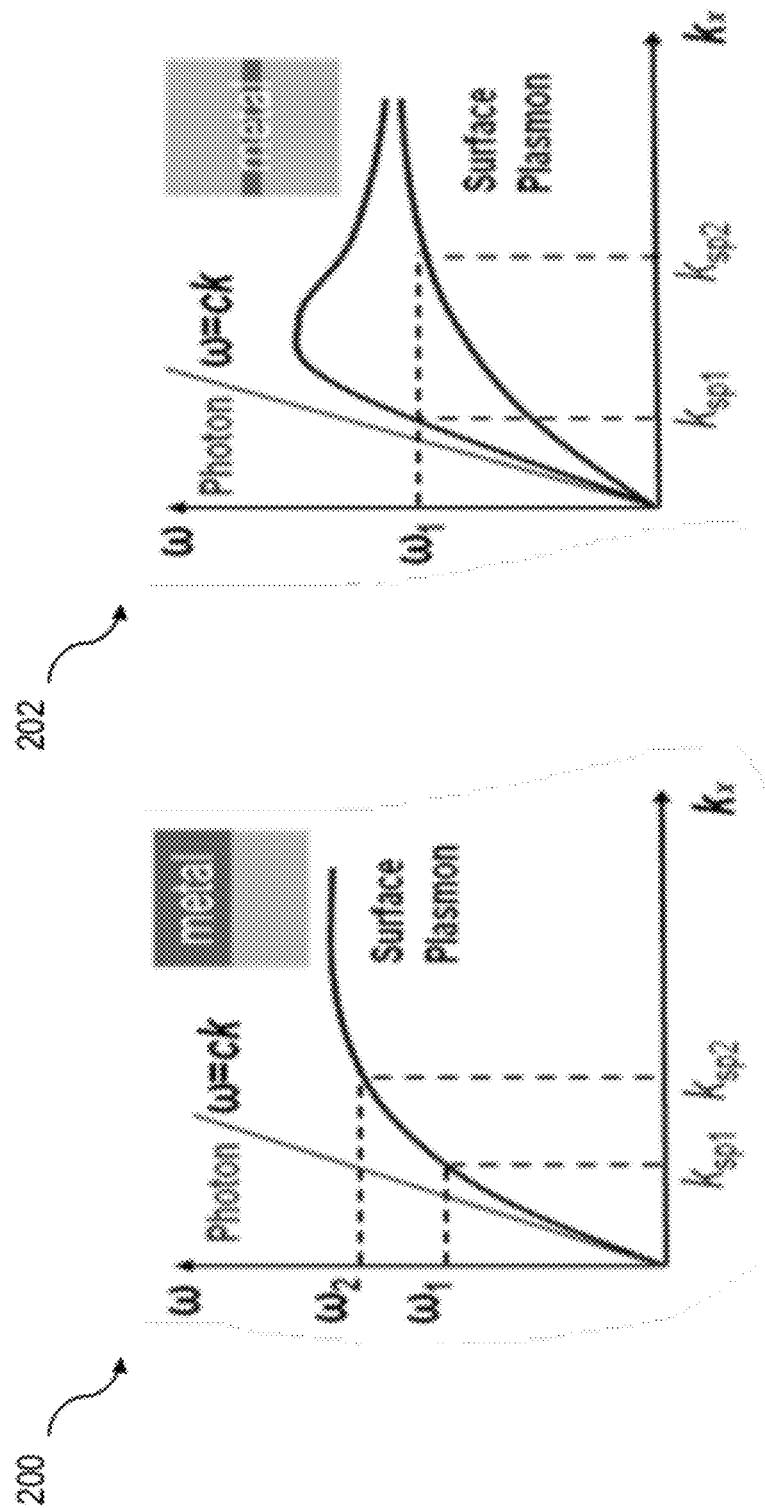

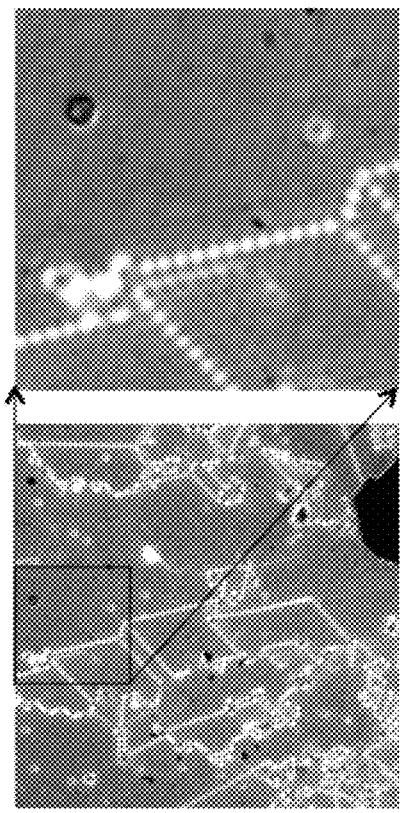
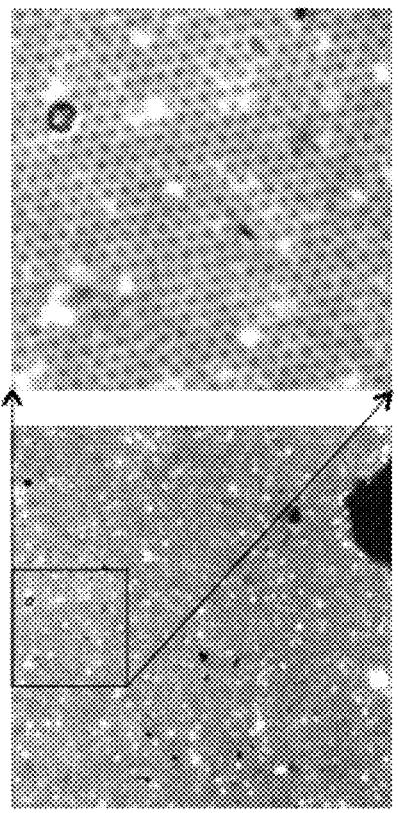
FIG. 3A
FIG. 3B

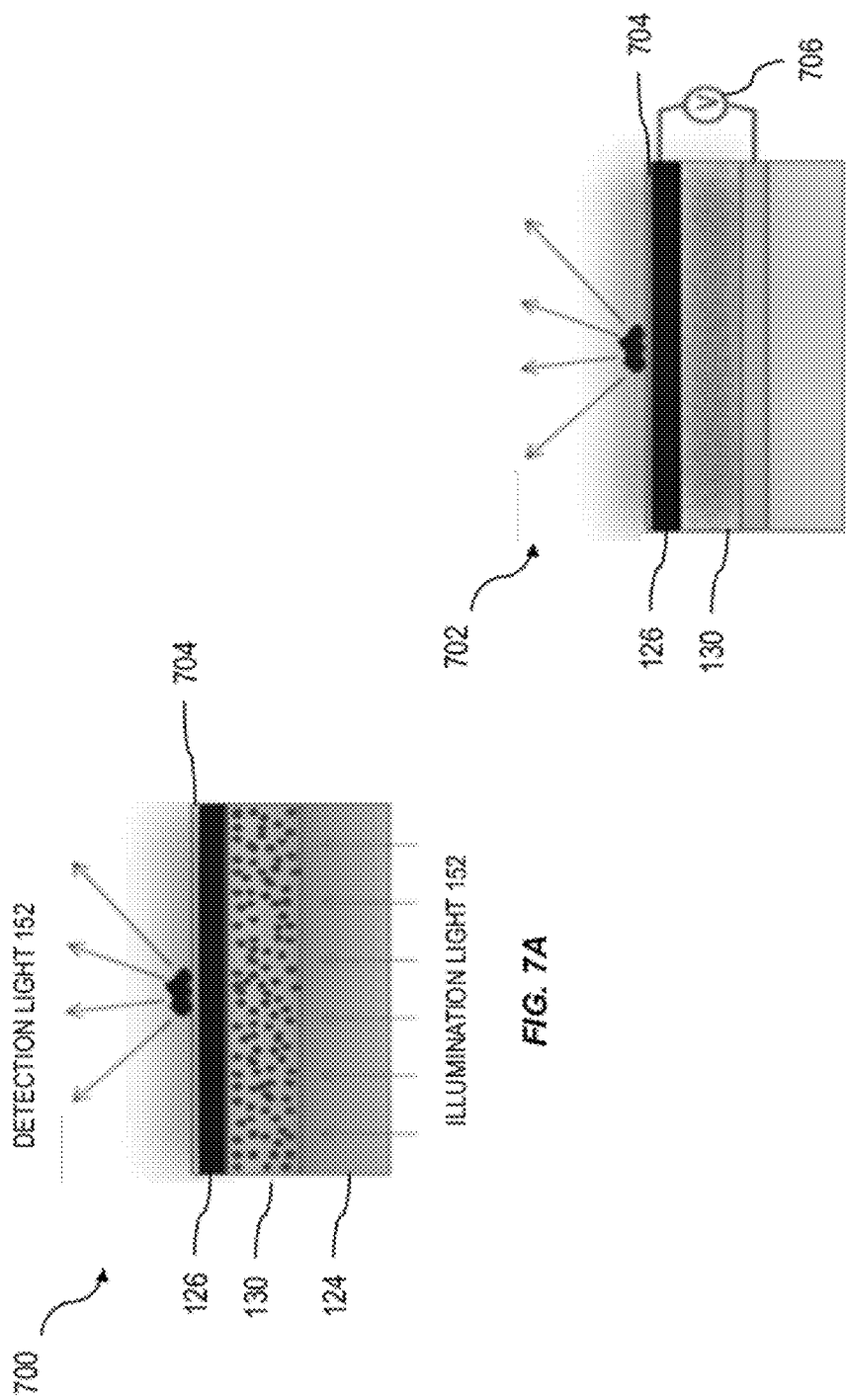

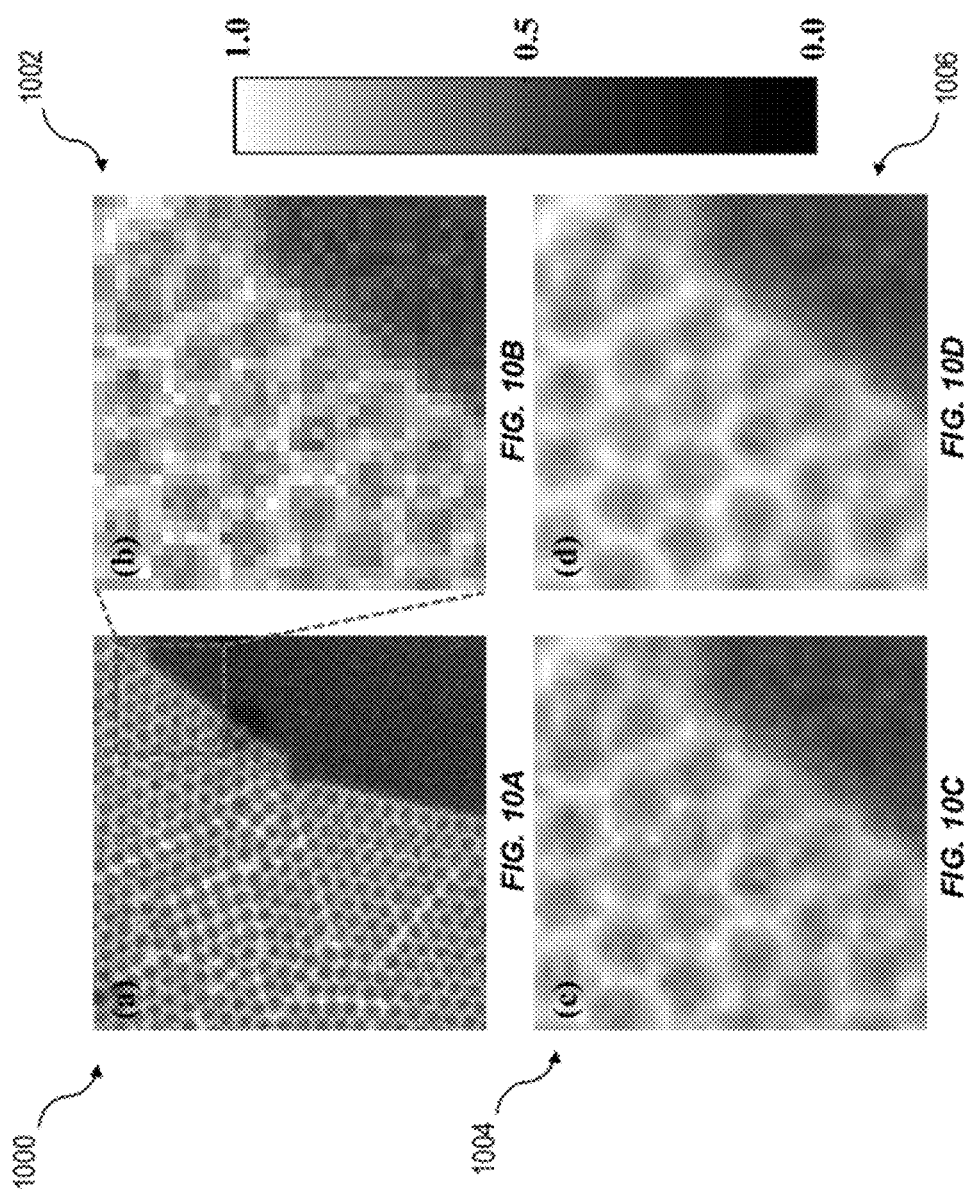

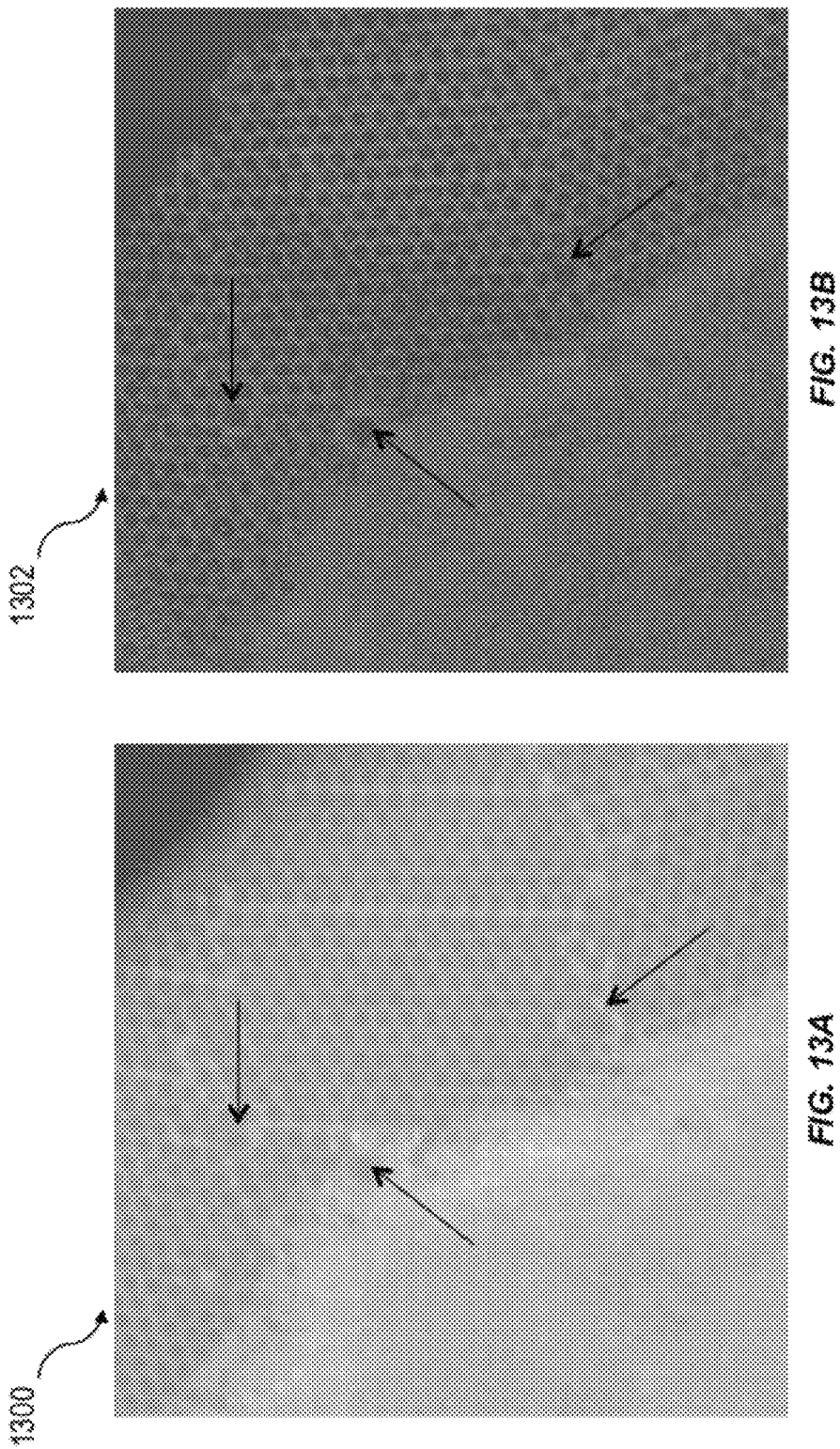

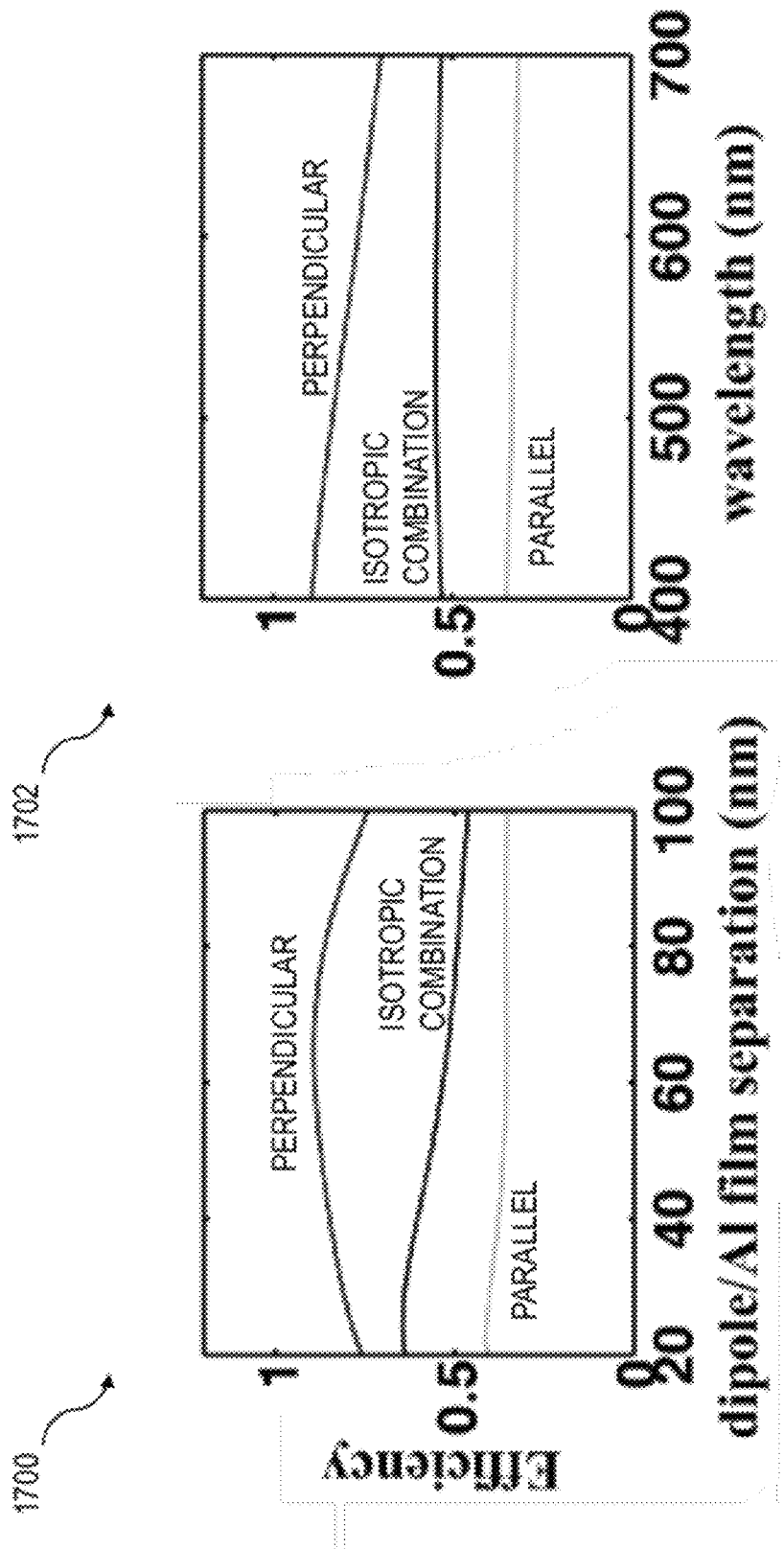

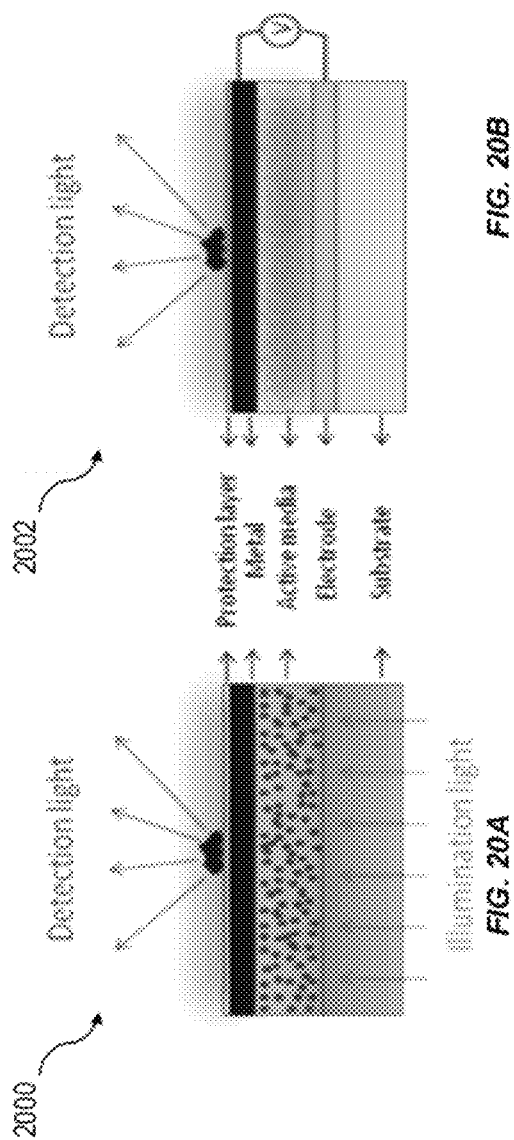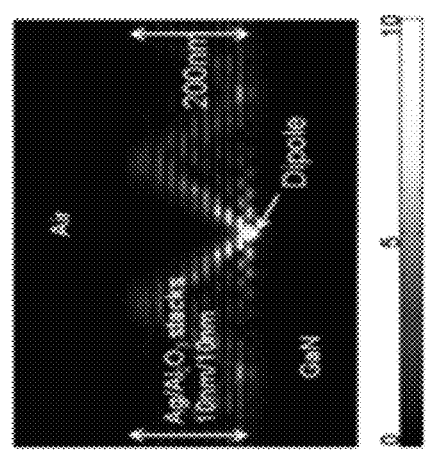
FIG. 20A
FIG. 20B
FIG. 20C

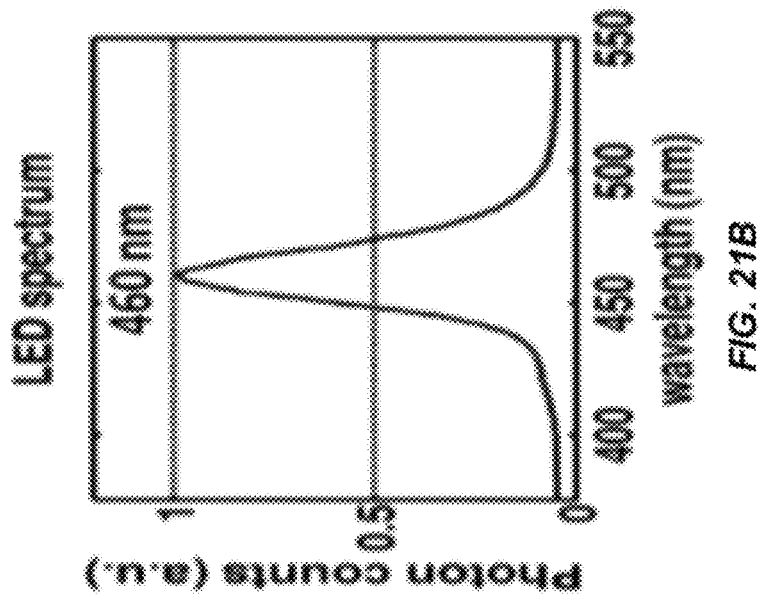
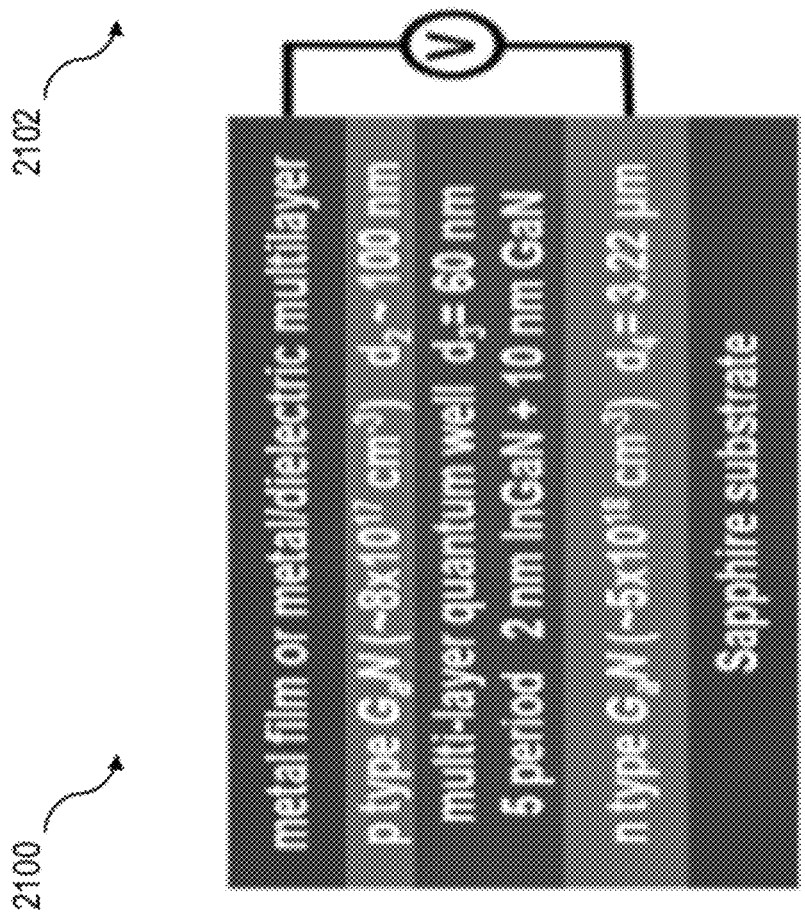
FIG. 21A
FIG. 21B

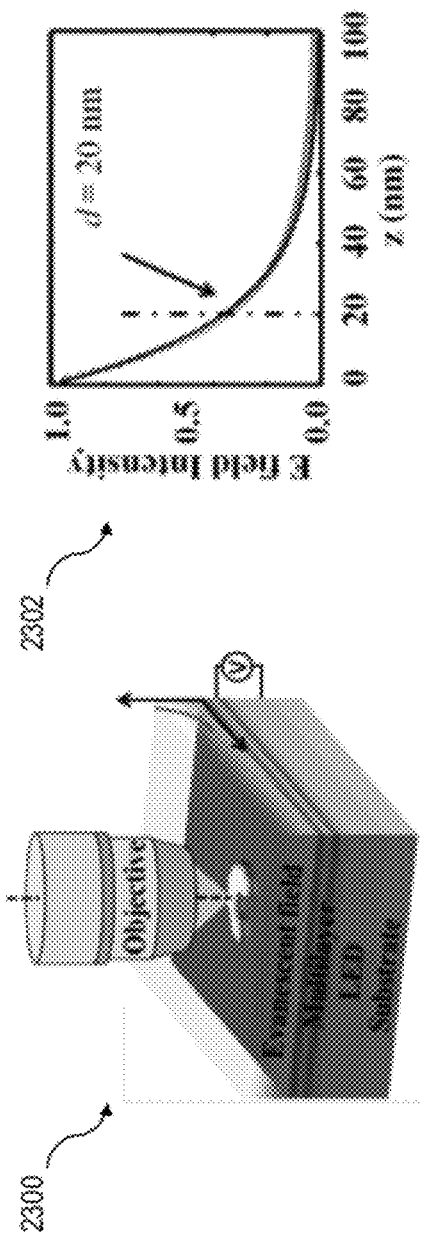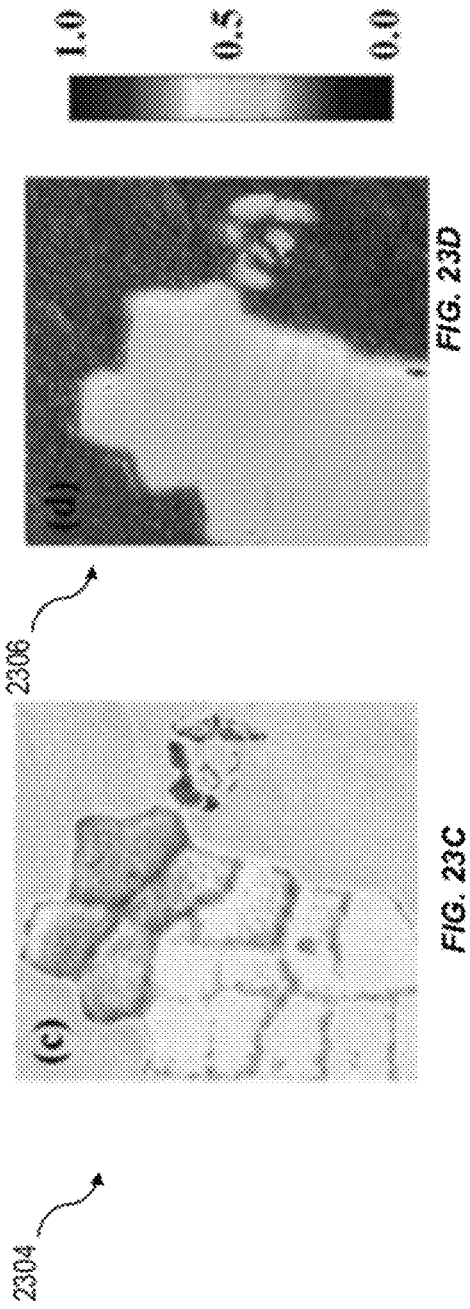
FIG. 23A
FIG. 23B
FIG. 23C
FIG. 23D

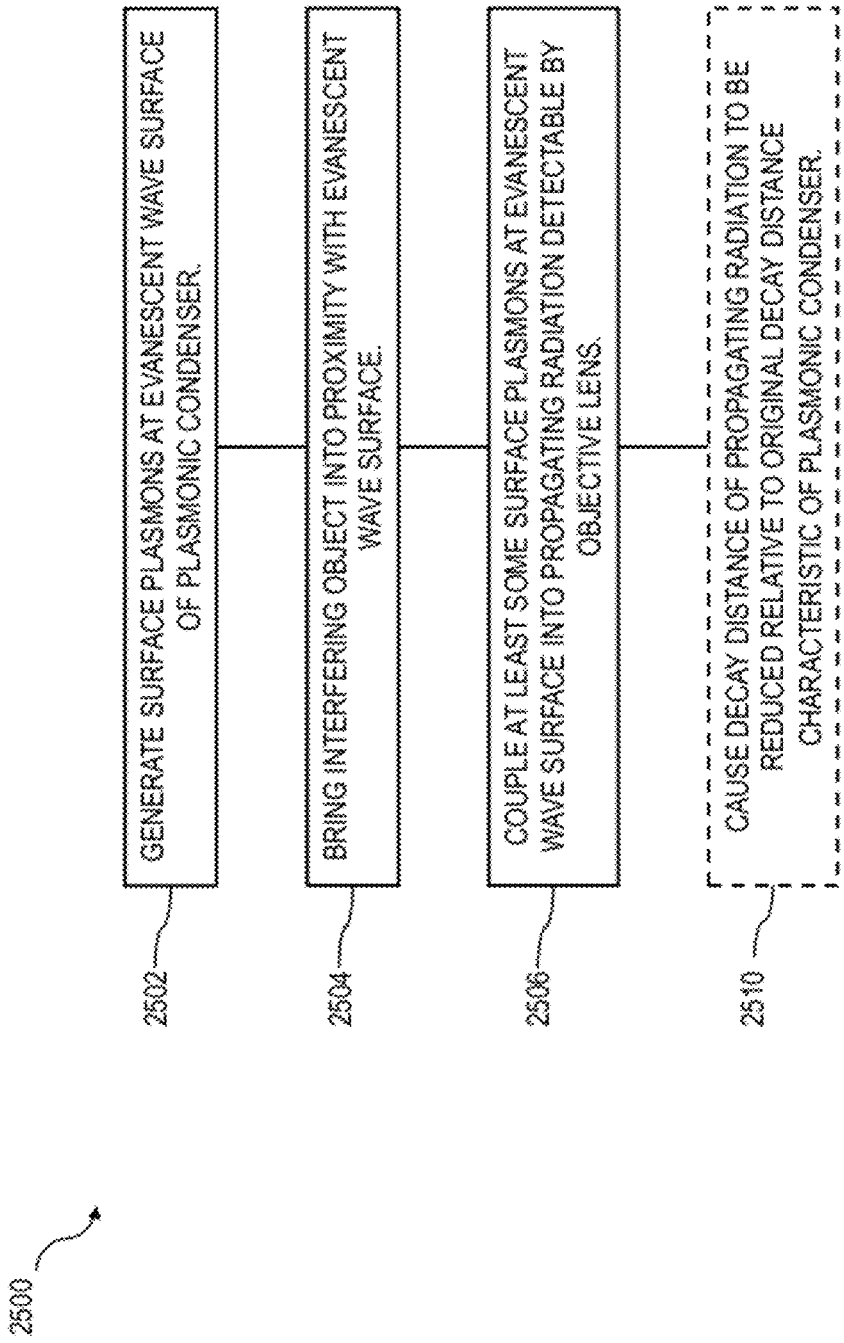

PLASMONIC DARK FIELD AND FLUORESCENCE MICROSCOPY

CROSS-REFERENCE TO RELATED APPLICATION

The current application claims priority under 35 U.S.C. §119(e) to U.S. Provisional Application No. 61/451,504, filed on Mar. 10, 2011, the disclosure of which is incorporated herein by reference in its entirety.

TECHNICAL FIELD

The subject matter described herein relates to microscopy in general. More particularly, at least some implementations relate to one or both of dark field microscopy and wide field fluorescence microscopy.

BACKGROUND

The optical microscope remains an irreplaceable tool for life science research even today, because light is often the best way to examine living cells non-invasively. As a special optical imaging technique, dark field (DF) microscopy enables the creation of high contrast images of unstained transparent specimens. In order to form a bright specimen image on a dark background, oblique rays from every azimuth are allowed to strike the samples but only light scattered from the specimens are collected by the objective. In other words, dark field (DF) microscopy works on the principle of illuminating a sample with light that will not be collected by the objective lens, and that will therefore not form part of the image. Consequently, the dark field image appears as a dark, almost black background with a bright object on it. Conventional approaches to DF microscopy typically involve an optical condenser capable of focusing light at a specific angle to the sample, and an objective that excludes the directional transmission of light through the sample.

Wide field fluorescence microscopy includes techniques that conventionally rely on illumination of fluorophore-labeled specimens with a broad cone of light. The limited spatial resolution demonstrated by wide field fluorescence microscopy, especially along the optical axis (referred to as "Z-resolution"), can create challenges in differentiating between individual specimen details that are overpowered by background fluorescence outside of the focal plane.

SUMMARY

In one aspect, an apparatus includes a plasmonic condenser for generating surface plasmon at an evanescent wave surface. The plasmonic condenser includes a substrate layer, a metal layer comprising the evanescent wave surface, and a media layer disposed between the metal layer and the substrate layer. The media layer includes a source of radiation that can interact with the metal layer to create surface plasmons that are not substantially optically detectable as far field radiation until an interfering object is brought into proximity with the evanescent wave surface. When such an interfering object is brought into proximity with the evanescent wave surface, it causes coupling of at least some of the surface plasmons into propagating radiation optically detectable by an objective lens.

In an interrelated aspect, a method includes generating surface plasmons at an evanescent wave surface of a plasmonic condenser. The evanescent wave surface includes a metal layer that further includes the metal layer, a substrate layer, and a media layer disposed between the metal layer and the substrate layer. The media layer includes a source of radiation that interacts with the metal layer to create the surface plasmons that are not substantially optically detectable as far field radiation. The method further includes bringing an interfering object into proximity with the evanescent wave surface and coupling at least some of the surface plasmons at the evanescent wave surface into propagating radiation optically detectable by an objective lens, the coupling comprising the surface plasmons interacting with the interfering object.

In some variations one or more of the following can optionally be included. The apparatus can optionally further include the objective lens. The metal layer can optionally have sufficient thickness to serve as an attenuator to prevent directional transmission of the radiation from the source through the metal layer. The metal layer can optionally have a thickness in a range of approximately 10 nm to 150 nm or optionally of approximately 50 nm to 150 nm. The media layer can optionally include a fluorescent dye that emits the radiation at one or more transition wavelengths upon being excited by incident light provided via the substrate. The media layer can optionally include a coupling grating disposed beneath the metal layer. The coupling grating can optionally include a grating period that results in at least partial conversion of the radiation at one or more wavelengths into the surface plasmons upon being struck by incident light provided via the substrate. The media layer can optionally include at least one of a light emitting diode and an organic light emitting diode that emits the radiation at one or more wavelengths upon experiencing an applied voltage. The radiation can optionally be directly coupled into the surface plasmons. The metal layer can optionally serve as an electrode via which the applied voltage is delivered. A plasmonic meta-materials illuminator can optionally include the plasmonic condenser. The plasmonic meta-materials illuminator can optionally further include a plurality of layers of meta-materials overlaying the metal layer. The plurality of layers of meta-materials can optionally cause a decay distance of the propagating radiation to be reduced relative to an original decay distance characteristic of the plasmonic condenser.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings, FIG. 1A, FIG. 1B, and FIG. 1C show diagrams illustrating features of a conventional dark field microscopy configuration (FIG. 1A), a plasmonic dark field microscopy configuration (FIG. 1B), and a configuration of a plasmonic condenser FIG. 1C;

FIG. 2A and FIG. 2B show two charts illustrating typical surface plasmon dispersion curves at a semi-infinite metal-dielectric interface (FIG. 2A) and a thin metal film (FIG. 2B);

FIG. 3A and FIG. 3B show images obtained by conventional dark field microscopy and the plasmonic dark field microscopy, respectively;

FIG. 7A and FIG. 7B show diagrams illustrating features of two examples of active plasmonic condensers: a light pumped plasmonic condenser (FIG. 7A) and an electrical pumped plasmonic condenser (FIG. 7B);

FIG. 10A, FIG. 10B, FIG. 10C, and FIG. 10D show a microscopy image of self-assembled polystyrene particles and enlargements and enhancements thereof obtained using an OLED-based plasmonic condenser;

FIG. 13A and FIG. 13B shows images of a polystyrene bead lattice, obtained using conventional dark field microscopy and plasmonic dark field microscopy, respectively;

FIG. 17A and FIG. 17B respectively show graphs illustrating dipole SP coupling efficiency with respect to dipole metal film separation at 400 nm emission wavelength (FIG. 17A) and averaged coupling efficiency for dipole/metal film distance from 20-60 nm with respect to emission wavelength (FIG. 17B), for a perpendicular dipole orientation, a parallel dipole orientation, and an isotropic combination respectively.

FIG. 20A and FIG. 20B are diagrams respectively showing a fluorescent dye-based active plasmonic meta-materials illuminator, a LED-based plasmonic meta-materials illuminator, and FIG. 20C is a graph showing results of a numerical simulation of the near-field coupling between a dipole and a Ag/Al$_2$O$_3$ multilayer meta-material with a distance between the dipole and the meta-material of 10 nm and a wavelength of 460 nm;

FIG. 21A and FIG. 21B respectively show a diagram of a layered structure of a plasmonic meta-materials illuminator (PMI) using a GaN blue LED and a graph of a LED emission spectrum with a peak of the spectrum around 460 nm with an approximately 26 nm bandwidth (FWHM);

FIG. 23A, FIG. 23B, FIG. 23C, and FIG. 23D respectively show a schematic configuration of a LED-based plasmonic metamaterials illuminator (PMI), a graph of a numerical simulation of the decay length of the evanescent field generated at the multilayer/air interface, and two images showing a comparison of the scattering image of 200 nm self-assembled particles using conventional reflection dark-field microscopy and LED-based meta-materials mediated evanescent wave (MMEW) microscopy through the LED based PMI;

FIG. 25 is a process flow diagram illustrating aspects of a method having one or more features consistent with implementations of the current subject matter.

When practical, similar reference numbers denote similar structures, features, or elements.

DETAILED DESCRIPTION

Figure 4:
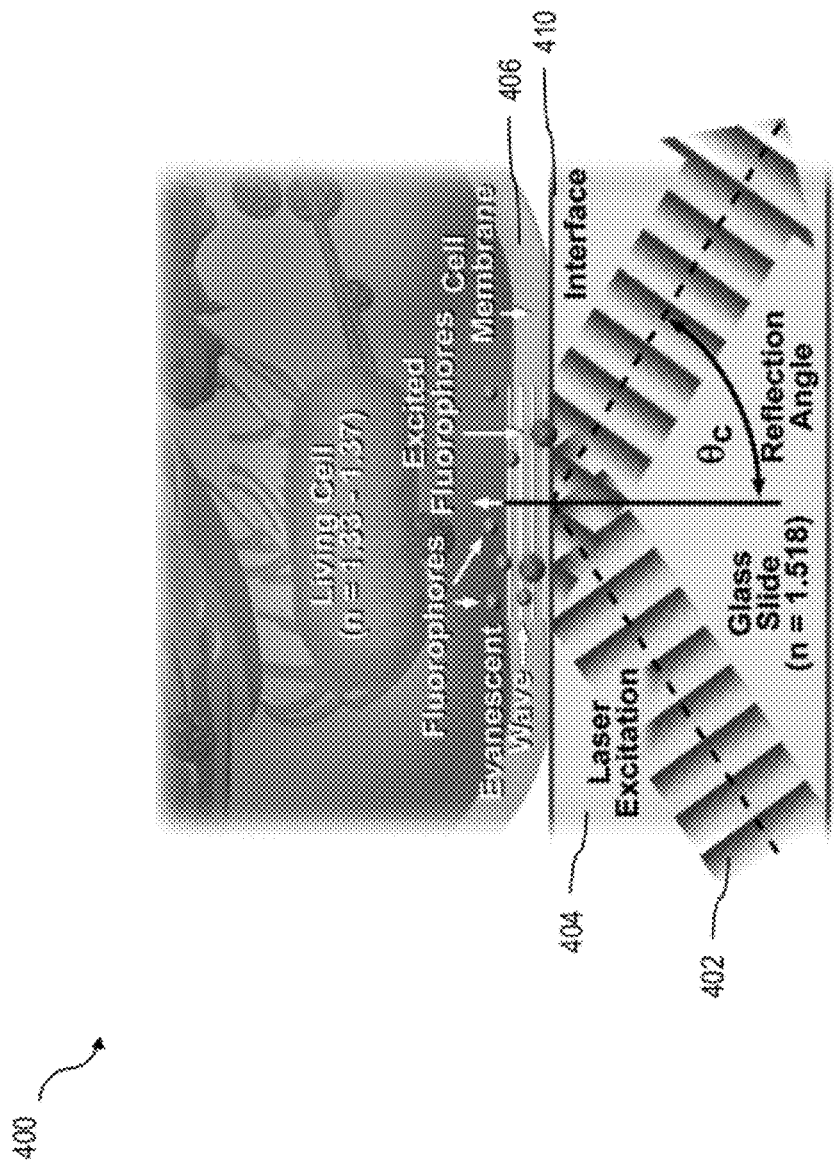
FIG. 4 shows a diagram illustrating features of total internal reflection microscopy.

In a conventional DF microscopy apparatus 100, an example of which is illustrated in FIG. 1A, the central part of the cone of the illumination light 102 provided by the condenser 104, which ordinarily passes through and around the sample or specimen 104, is blocked by a light stop 108, allowing only oblique rays to strike the sample 104 on the microscope slide 110. This blocking of the central part of the illumination light can be helpful if the sample objects have refractive indices very close to that of their surroundings and are difficult to image using conventional bright field microscopy. While conventional DF microscopy can achieve high contrast imaging, its resolution can also be further improved using a high numerical aperture (NA) configuration of a paired condenser 104 and objective 112. However, the NA of the objective 112 must generally be smaller than that of the condenser 104 to prevent the oblique illuminating rays from entering the objective 112 and thereby allow only diffracted light 114 to enter the objective 112. In addition, a high NA condenser 104, such as a cardioid condenser, can generally be highly sensitive to alignment and thus must be accurately positioned and aligned to a very sharp cone of illumination, which can require a relatively high level of expertise for proper use. In addition, the illumination light in such a high NA arrangement must be very strong due to the sharp illumination cone 102, which can be wasteful of energy. In short, conventional DF microscopy approaches are generally instrumentally complex, costly, and bulky.

Approaches to DF microscopy consistent with implementations of the subject matter herein can utilize a chip-scale integrated plasmonic multilayered structure as a substitute for the bulky and expensive conventional condenser optics noted above. The chip-scale integrated plasmonic multilayered structure described further below is also referred to herein as an "a plasmonic condenser (PC)" and the imaging technology associated with this approach is referred to herein as plasmonic dark field (PDF) microscopy. An example of a DF microscopy apparatus 120 consistent with an implementation of the current subject matter is schematically shown in FIG. 1B, in which a plasmonic condenser (PC) 150 replaces the conventional condenser 104 shown in FIG. 1A. The PC 150 can, as shown in FIG. 1B, include a substrate 124 and a metal surface layer 126 with an active media layer 130 disposed between the substrate 124 and the metal surface layer 126. Unlike in the conventional apparatus 100, a light stop 108 is not required, and the sample or specimen 106 can be placed directly on the metal surface layer 126.

As described herein, a plasmonic condenser 150 uses surface plasmons (SPs), which can also be referred to as surface plasmon polaritons (SPPs), to illuminate a sample. SPs, which are surface electromagnetic waves formed by collective oscillation of electrons at a metal/dielectric interface, can possess wave vectors (k-vectors) much higher than the photons at the same frequencies. Fundamental properties of SPs have been extensively studied and widely applied in a number of important applications such as surface plasmon resonance (SPR) sensing and imaging (SPM), surface enhanced Raman scattering (SERS), surface enhanced second harmonic generation, surface enhanced fluorescence, and the like.

The dispersion relation for the SPs at an interface between semi-infinite metal and dielectric materials can be written as:

$$k_{sp} = \sqrt{\frac{\varepsilon_l \varepsilon_m}{\varepsilon_l + \varepsilon_m}} \frac{2\pi}{\lambda_0} \quad (1)$$

where $k_{sp}$ is the SP wave vector, $\lambda_0$ is the light wavelength in vacuum, and $\varepsilon_l$ and $\varepsilon_m$ are the permittivity of the dielectric and metal, respectively. FIG. 2A and FIG. 2B show graphs 200 and 202, which respectively illustrate two typical dispersion curves of surface plasmons. The curves in the graph 200 of FIG. 2A are described by Equation 1. As shown in FIG. 2A and FIG. 2B, all of the SP dispersion curves lie to the right of the light cone, indicating that the SPs always have a larger wave vector, or smaller wavelength, than light at the same frequency. At some conditions, the wavelength of the SPs is extremely small. The smaller the wavelength, the higher the potential spatial resolution can be achieved when the corresponding SPs are used as the probing field to interact with a specimen of interest.

Referring again to FIG. 1B, generated SPs are evanescent on the metal surface 126 and cannot be directly detected in the far field by a conventional objective lens 112. However, when one or more objects (e.g. objects of a sample or specimen 106) are brought to the vicinity of a metal surface 126 with excited SPs, the SPs are scattered to the far field and thus become optically detectable. Meanwhile, in the areas of the metal surface 126 that are not in contact with the one or more objects of a sample or specimen 106, the SPs remain evanescent and thus not substantially optically detectable in the far field. In this manner, a high contrast DF image of the one or more sample objects in the far field can be formed without interfering light away from the object. Generally, a PC 150 includes a thin surface layer of metal 126 integrated with one or more additional features that provide a mechanism for SP excitation. Potential examples of SP excitation mechanisms include, but are not limited to, quantum dots, photoluminescent and electroluminescent materials, a diffraction grating, and the like disposed proximate to a thin layer of plasmonic metal 126 to excite SPs using their near field. As used herein, the terms "not detectable," "not optically detectable," "not substantially optically detectable," and the like when used to describe surface plasmon properties generally refer to the to the existence of surface plasmons as coherent electron oscillations at an interface between two materials. These coherent electron oscillations generally propagate along the interface in an optically undetectable manner until coupling with an object or other interference at the surface results in the release of photons that can be detected in the far field.

In one example of an implementation of the current subject matter, a device for plasmonic dark field (PDF) microscopy can include a chip-scale integrated active PC 150 based upon a fluorescent dye, such as for example Rhodamine 6G, as the active media 130. Illustrative features of such an active PC 150 are shown schematically in FIG. 1C. As shown in FIG. 1C, a plasmonic condenser 150 can include a three-layer structure, which can further include an active layer 130, which can in one example include a mixture of polymethyl methacrylate (PMMA) and Rhodamine 6G molecules sandwiched between a glass substrate 124 and a thin layer of silver 126.

As shown in FIG. 1C, illumination light 152 provided from below or otherwise via the glass substrate 124 can excite the dye molecules in the active media layer 130 to create SPs in the metal surface layer 126. Contact of one or more sample or specimen objects 106 with the metal surface layer 126 can cause emission of visible far field detection light 154, which can be viewed via the objective (not shown in FIG. 1C). Because the detectable light from the PC 150 is created only by conversion of SPs into far field light due to interaction of a sample or other object on the metal surface 126, plasmonic dark field microscopy only exists at the interface of the PC 150 in the form of SPs. The depth of field and the sensitivity of the PDF microscopy along the direction normal to the surface of the PC 150 are determined by the decay property of the SPs.

Due to differences between SPs and conventional illumination light, the image information obtained using conventional DF microscopy and PDF microscopy are different. FIG. 3A and FIG. 3B show the images of a sample of two layers of about 2-µm polystyrene beads obtained using the conventional DF microscopy and the PDF microscopy, respectively. The image 300 in FIG. 3A, which was prepared by conventional DF microscopy, mainly provides contrast at the top layer while the PDF image 302 reveals the bottom layer with much more improved contrast. It should be noted that the additional layer of particles does not affect the image quality much in the PDF microscopy.

PDF microscopy using a chip-scale integrated multilayered fluorescent active PC is described and demonstrated herein. This approach can also be extended to other types of PCs as mentioned above and discussed in further detail below. Techniques described herein in reference to PDF microscopy can also be applied to fluorescence microscopy, which is similar to the extension of total internal reflection (TIR) microscopy to total internal reflection fluorescence (TIRF) microscopy. Because SPs can have high k-vectors, high resolution beyond the diffraction limit can also be obtained with compact and low-cost PDF microscopy. The PDF technology described herein can provide superior contrast imaging capability for thin samples than conventional DF microscopy. Finally, because a plasmonic condenser 150 consistent with implementations of the current subject matter can be planar, PDF microscopy can be practiced without concern for complicated alignment procedures typically required in conventional microscopy approaches.

A PDF approach consistent with implementations of the current subject matter represents a revolutionary break with the framework of conventional dark field lens design. Instead of using mirrors and lenses to guide the illumination angle of the light, a metallic structure is introduced to convert the light into surface plasmons. As the surface plasmons exist only at the metal surface 126, the metal surface can appear completely dark in the far field. Only when an object (e.g. a sample, a specimen, etc.) is brought to the near field of the metal surface 126, is the light coupled into far field to form a perfect dark field image. Both the light illumination angle and the NA of the detection objective can determine the spatial resolution of the dark field microscopy. In conventional dark field microscopy, the NA of the objective cannot be fully utilized, as the directional transmission from the condenser must be blocked. This can result in compromising the resolution to create a proper dark background. For a PDF approach as discussed herein, the detection NA can be fully used, as the background is automatically dark. The surface plasmons have much higher in-plane wave vectors than light at any possible incident angles. These special properties boost the resolution for PDF microscopy. Surface Plasmon waves only exist at the near field of the metal surface, which is invisible at the far field. In principle, the background of the PDF microscopy should be completely dark regardless of the NA of the detection objective. In PDF microscopy, the illumination light source and the condenser can be readily integrated into a single unit, which differs substantially from the level of complexity inherent with conventional approaches. For instance, the plasmonic structure can be deposited on top of a LED or an OLED surface as discussed in further detail below. In these examples, light can be directly coupled into the surface plasmons before it irradiates out light to the space. When electrical power is provided, the surface plasmons can be excited on the metal surface. If an object sits on the lens surface, a superior dark field image will form. There is no light in the whole space if no scattering object is close to the lens, as if the power of the light source is off. This is a further evidence for the super contrast.

An objective lens produced for use in PDF microscopy consistent with implementations of the current subject matter can be produced in large quantities by standard procedures such as film coating and deposition and can have an associated low cost to produce when compared to bulky components that include multiple lenses and mirrors typically required for conventional dark field microscopy.

As noted above in reference to FIG. 1A, conventional dark field microscopy is generally performed using an illumination condenser and detection objective. These two components are paired, and the NA for the detection objective is typically smaller than that of the condenser. The condenser is typically big and bulky (~cm scale), and the objective 112 is typically specially designed (i.e. a dark field objective). In contrast, PDF microscopy approaches consistent with the descriptions herein use a plasmonic condenser 150, which can generally include a few layers of thin materials. The total thickness of the operative parts of such a device can in some implementations be at a fraction of a micrometer or smaller scale.

An active PC 150 such as that illustrated in FIG. 1C can be fabricated using standard micro fabrication techniques. In one illustrative example, Rhodamine 6G molecules can be first mixed with PMMA at a concentration of approximately $10^{-4}$ mol/L. Then the mixture can be spin coated on a cover glass substrate. After a soft bake process, which can last approximately 2 minutes in this example, an approximately 150 nm thick layer mixture as the active layer can be obtained. Finally, about 60-nm thick silver film can be deposited on top of the PMMA using an E-beam evaporation method or other approach.

Total internal reflection fluorescence microscopy (TIRF) is an elegant optical technique utilized to observe single molecule fluorescence at surfaces and interfaces. It allows extremely thin optical sectioning, typically with a lower Z-resolution limit of about 100 nm and excellent signal-to-noise ratios. TIRF is often employed to investigate the interaction of molecules with surfaces, an area that is fundamentally important to a wide variety of disciplines in cell and molecular biology. Examples are binding and triggering of cells by hormones, neurotransmitters, and antigens; cell adhesion to surfaces; electron transport in the mitochondrial membrane; cytoskeletal and membrane dynamics; and cellular secretion events.

TIR and TIRF can be considered a special case of dark field microscopy. TIRF microscopy can provide valuable advantages relative to other approaches due to the induced evanescent waves, in which the electric field vector exponentially decays with distance from the EW capture surface. In TIRF microscopy, such evanescent waves can be generated from total internal reflection of illumination light. For total internal reflection to occur, several criteria must be met, for example as illustrated in the diagram 400 of FIG. 4. The excitation light beam 404 must pass through high refractive index (RI) media (for example an immersion oil/coverglass having a RI~1.518) 404 to a lower RI medium (for example an aqueous mounted specimen with RI=1.38) 406. The excitation light must strike the interface 410 between these media at an angle of incidence that is equal to or greater than the critical angle ($\theta_c$), which is defined in equation 2 (see below) as the incidence angle beyond which no light passes from the high refractive index media ($n_1$) 404 to the lower refractive index media ($n_2$) 406. Under such conditions, all of the light is internally reflected within the high refractive index media 404. Even though 100% of the excitation light is reflected, an electromagnetic field vector is propagated into the lower RI media 406, in this example the region beyond the interface 410 formed at the edge of the cover slip. The intensity distribution $I_z$ of the evanescent fields and its decay length (d, where the initial intensity decreases to $1/e \approx 37\%$) depends on refractive indices of both mediums 404, 406 as well as the free space wavelength ($\lambda_0$) and angle of the incident light ($\theta > \theta_c$) as indicated in equation 3 and equation 4 below.

$$I_z = I_0 e^{-z/d} \tag{2}$$

$$d = \frac{1}{2k_z} \tag{3}$$

$$= \frac{\lambda_0}{4\pi\sqrt{NA^2 - n_2^2}}$$

$$= \frac{\lambda_0}{4\pi\sqrt{n_1^2 \sin^2\theta - n_2^2}}$$

$$= \frac{\lambda_0}{4\pi\sqrt{n_1^2(\sin^2\theta - \sin^2\theta_c)}}$$

$$\theta_c = \mathrm{Sin}^{-1}(n_1/n_2) \tag{4}$$

where $k_z$ is the imaginary part of the wave vector along the Z-direction and $I_0$ is the intensity of the incident light at the interface.

Fluorophores residing near the glass-liquid surface (~100 nm) can be excited by the evanescent field, provided they have electronic transitions that occur in or very near the wavelength bandwidth of the illuminating light beam. Because of the exponential falloff of evanescent field intensity, fluorophores farther away from the surface avoid being excited, which leads to a dramatic reduction of unwanted secondary fluorescence emission from molecules that are not in the primary focal plane. Thus, TIRF microscopy has better z-axis resolution than other optical section microscopy such as confocal microscopy (100 nm vs. 500 nm). As a result, high-contrast images of surface events is produced with a significant increase in signal-to-background ratio over classical wide field techniques, which can improve the sensitivity of the system and the ability to view very dim fluorescence events. Moreover, because illumination is restricted to the interface regions and does not penetrate the specimen bulk, living cells tend to survive longer under fluorescence observation using TIRF microscopy techniques. This feature can facilitate increasing the length of observations as well as the performance of time-lapse cinemicrography for extended periods, often ranging for many hours or even one or more days.

Currently available TIRF microscopy techniques can remove background fluorescence outside the focal plane by employing the unique properties of an induced evanescent wave (EW) to selectively illuminate and excite fluorophores only in a very thin (e.g. less than about 100 nm) layer near the substrate, thereby avoiding excitation of fluorophores outside this sub-diffraction-limited optical section. Due to the rapid decay of the evanescent wave along the optical axis, TIRF microscopy has much better Z-resolution than other optical section microscopy such as confocal microscopy and multiphoton excitation microscopy, which typically have Z-resolutions of less than approximately 500 nm. TIRF microscopy techniques can be ideal for studying cellular membrane activities, the dynamics of filaments of actins or other proteins, cellular adhesion, movement, single molecule events, vesicle and protein tracking, or the like.

Moreover, to ensure total internal reflection, the incident angle should be larger than the critical angle, which can require expensive optical components (e.g. high NA objectives) that must be accurately positioned and aligned. For example, TIRF requires that the NA of the objective is larger than the refractive index of the medium that includes the objects to be imaged. Therefore, the lenses have to be construed of high refractive index materials. As the refractive index value for the good lens materials is limited, the NA for as TIRF objective is typically around 1.5 but not much larger. However, it can be extremely difficult if not impossible to perform TIR when the media index is very large. In addition, the light beam has to be adjusted very precisely with the incident angle larger than the critical angle. Therefore, other than a TIRF objective, a TIRF illumination light control module is used in practice. Such devices are generally quite very complicated, hard to adjust, and expensive.

The PDF microscopy approaches described herein do not suffer from one or more of the TIR and TIRF microscopy problems mentioned above. In the case of PDF microscopy, the surface plasmon waves are always evanescent at the PDF lens surface regardless of the media refractive index. At the same light frequency, the surface plasmon waves possess much higher in-plane wave vector than that of light at any possible incident angles. This characteristic also causes a PDF lens to have much better resolution than a comparable TIR lens because there is no need of any special control of incident light. Any light illuminated on the PDF lens can excite surface plasmons. In fact, the PDF lens can be designed by using electrical excitation rather than light.

Surface plasmons (SPs) are mixture of electromagnetic (EM) waves and collective oscillation of free elections at a metal/dielectric interface. Because the wave vector of SPs is always larger than that of EM waves in the dielectrics, the SPs are often termed as evanescent surface plasmons indicating that the SPs only exist on the interface and decay exponentially away from it. For the same reason, the conversion between light and the SPs generally must be assisted by a coupling element such as a grating or high refractive index prism to compensate the wave vector or momentum mismatch. In other words, SPs are invisible in the far field if there is no coupling element. It is perfect from a dark field microscopy point of view if the surface plasmon is used as the probe instead of light. In the absence of any objects within the SP evanescent field region, the background signal is effectively non-existent. An object, when is brought into the SP field region, acts as a coupler and converts some portion of the SP energy into propagating light to form a bright imaging in the dark background. This is exactly the essence of dark field microscopy.

An element to realize the aforementioned properties should provide SP probing signals at its surface. As noted above, this device or apparatus can be termed a "plasmonic condenser" 150 with respect to its similar functionalities with a light condenser. Because of the dark field requirement, in general SP waves do not leak to propagation light without an object on the plasmonic surface. Therefore, the surface of the plasmonic condenser is advantageously flat with minimum surface roughness. In general, a plasmonic condenser 150 can be a passive plasmonic condenser or an active plasmonic condenser. Alternatively, a plasmonic condenser 150 can include both passive and active features.

Figure 5:
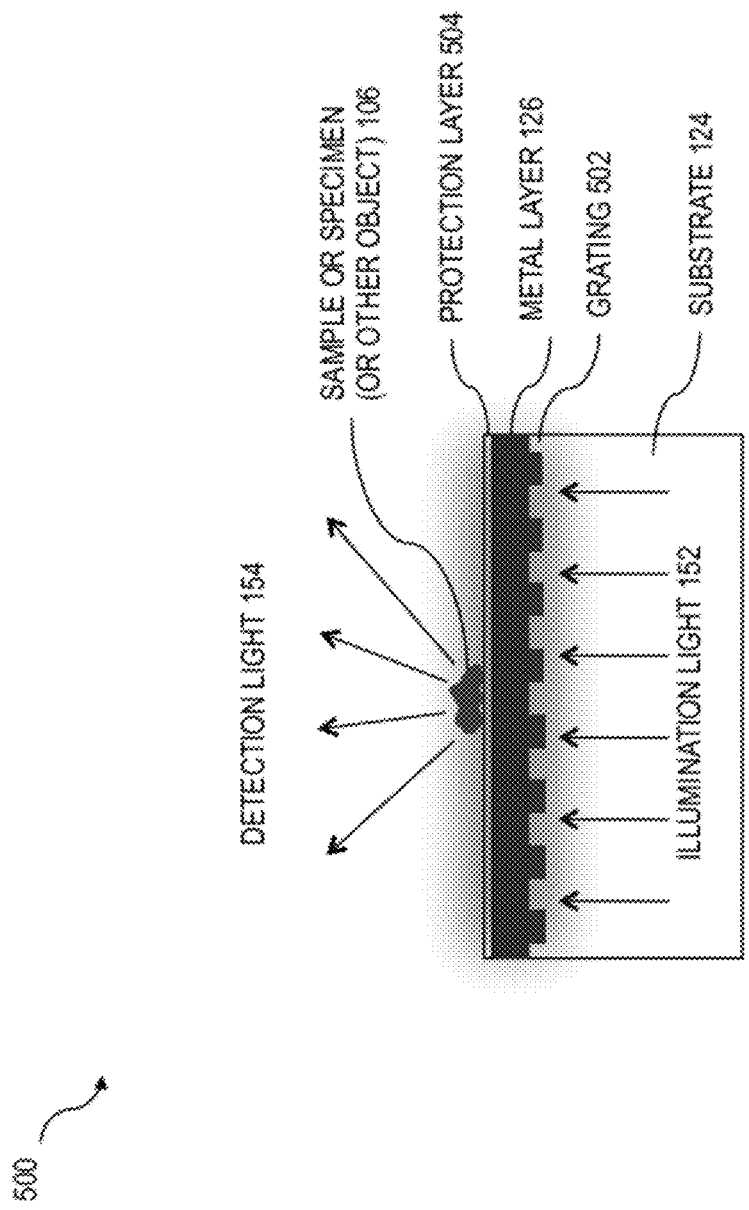
FIG. 5 shows a diagram illustrating features of a configuration of an example of a passive plasmonic condenser.

A passive plasmonic condenser involves a passive plasmonic structure to convert incident light into SP waves on its surface. FIG. 5 shows a diagram of an example passive plasmonic converter 500 in which illumination light 152 is provided from within a substrate or substrate layer 124 such that the illumination light 152 is incident on a grating 502, such as for example a coupling grating disposed beneath a metal layer 126 overlaid by a protective layer 504. For an appropriately designed grating period, the incident light is at least partially converted into SPs when the illumination light beam 152 shines on the coupling grating 502. In general, the grating period should advantageously satisfy the equation 5 below $$\frac{2\pi}{\lambda_{sp}} = \frac{2\pi}{\lambda_0}\sin\theta + n\frac{2\pi}{\Lambda} \text{ where } \lambda_{sp} = \sqrt{\frac{\varepsilon_d \varepsilon_m}{\varepsilon_d + \varepsilon_m}} \quad (5)$$

in which $\lambda_{sp}$ and $\lambda_0$ are the wavelength for the SP waves and light in vacuum respectively, $\theta$ is the incident angle, $\Lambda$ is the grating period, and n is an integer number. For instance, if the grating uses its first order to excite a normal incident light into SPs, the grating period $\Lambda$ should be equal to the SP wavelength, which is finally determined by the permittivity for the dielectric substrate and the metal, which are $\varepsilon_d$ and $\varepsilon_m$, respectively.

SP waves can be coupled from the bottom interface of the metal layer 126 to the top interface as shown in FIG. 5. In addition to acting as a plasmonic coupler, the metallic layer 126 can also serve as an attenuator to eliminate directional transmission of the illumination light through the passive plasmonic condenser 500. That is to say, the metal film thickness is advantageously optimized for both SP coupling and directional light blockage purposes. For a silver film, the metal layer can advantageously have a thickness in a range of approximately 10 nm to 150 nm, or alternatively, in a range of approximately 50 nm to 150 nm. In the absence of an object such as a sample or a specimen 106 that causes the SPs to be released as far field radiation, the SP waves are confined to the metallic structure 126 without any far field signal directed upwards along the optical axis. Presence of an object 106 causes scattering of at least some of the SPs into light, which can be detected as a dark field signal from above the passive plasmonic condenser 500. In practice, an optional protection layer 504 can be added on top of the metal film or metal layer 126 to make the plasmonic condenser 500 more compatible with biological or other potentially reactive materials. The protection layer 504 can optionally include one or more of glass, bio-friendly polymers, etc. Due to the passive nature of the structure, the excitation and the detection light generally has the same frequency characteristics. The illumination light 152 can be provided either by coherent lasers or incoherent lamps. The plasmonic structure simply converts the excitation light into SPs without altering much of the coherent properties. This provides possibilities for users to select an imaging mode, either single color coherent imaging or broadband white light imaging.

An active plasmonic condenser generally includes an active media capable of directly exciting SPs using excited electrons inside of an active media. One possible active medium is luminescent materials, for example including but not limited to photoluminescent materials, electroluminescent materials, bioluminescent materials, and chemiluminescent materials. Such media can further include one or more materials that are able to form on or both of coherent and incoherent light sources, for instance, fluorescent molecules, fluorescent polymers, ion doped crystals or glasses, semiconductor quantum well and quantum dot, semiconductor p-n junction, metallic cluster, and etc.

Figures 6A, 6B, 6C:
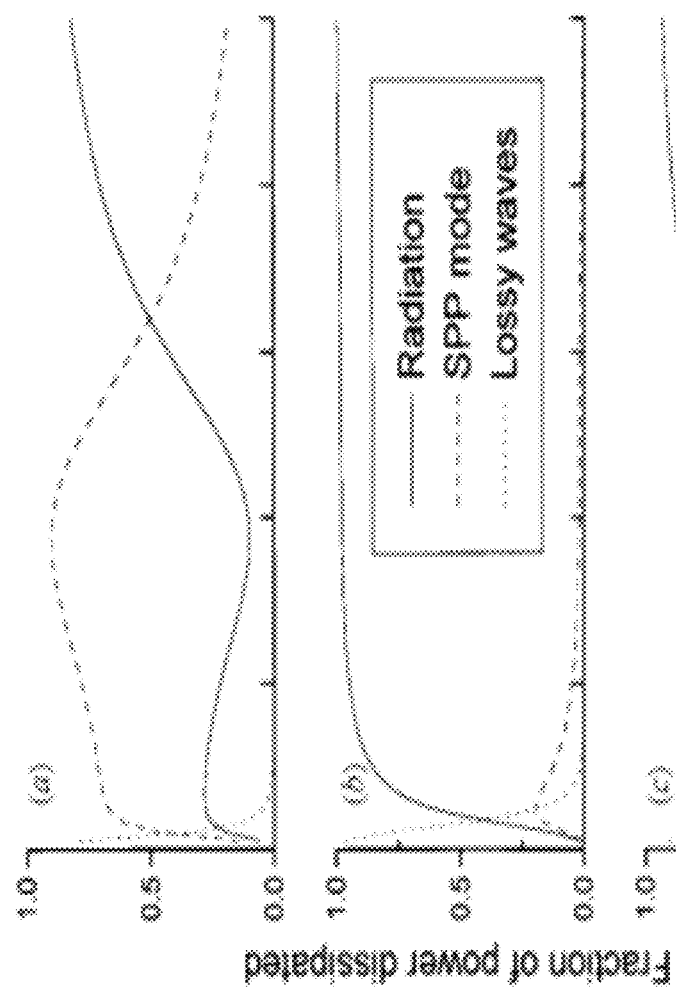
FIG. 6A, FIG. 6B, and FIG. 6C show graphs depicting the calculated fraction of power dissipated by an emitter in vacuum above an Ag mirror for a perpendicular dipole orientation (FIG. 6A), for a parallel orientation (FIG. 6B), and for an isotropic combination (FIG. 6C)

The coupling between an active medium and SPs can be modeled, for example by studying the coupling between a dipole in the vicinity of a metallic interface. FIG. 6A, FIG. 6B, FIG. 6C show charts 600, 602, and 604, respectively, which show calculated results regarding how much energy can be coupled into SPs when a dipole is placed with a distance d to the metal surface. The chart 600 in FIG. 6A shows the fraction of power dissipated by an emitter in vacuum above an Ag mirror for a perpendicular dipole orientation, the chart 602 in FIG. 6B shows the fraction of power dissipated by an emitter in vacuum above an Ag mirror for a parallel orientation, and the chart 604 in FIG. 6C shows the fraction of power dissipated by an emitter in vacuum above an Ag mirror for an isotropic combination. As shown in these graphs, for dipoles with isotropic orientations, about 40% of the energy is transferred into the SP mode when the d is between a few tens of nanometers to a few hundred nanometers. As discussed above, the function of the plasmonic structure is not only to support SP waves but also to block the directional transmission. In this case, the metal film needs to block about 60% of the residual light. This number thus provides a rough guideline for the metal thickness design. In some implementations, the metal film thickness can be in a range of approximately 10 nm to 150 nm, or alternatively, in a range of approximately 50 nm to 150 nm.

FIG. 7A and FIG. 7B show two example configurations of active plasmonic condensers 700 and 702. In the first active plasmonic condenser 700 of FIG. 7A, which is a light pumped plasmonic condenser, the active media layer 130 includes at least one kind of florescent dye molecules. When the florescent dye is pumped by light 152 at the dye's absorption frequency, the SPs will be excited at the dye emission frequency, which can be at a different wavelength (color) than the incident light 152. The directional transmission light at the emission frequency and pumping frequency is completely blocked by the metal film 126 or by an additional optical filter 704 as shown in FIG. 7A and FIG. 7B. In the second active plasmonic condenser 702 of FIG. 7B, the active media layer 130 can include a light emitting source such as a light emitting diode (LED) or an organic light emitting diode (OLED) that directly and actively emits light. When a voltage 706 is applied across the active media, SPs will be excited at the metal interface 126. In this configuration, light generated in the active media layer 130 can only leak out to the side and the bottom but not upward along the optical axis.

An active PC 700 based on stimulating emission of light from a dye via the injection of illumination light requires an external light source to excite the SP field, which can cause limitations in how compact such a system can be. Additionally, the use of dye molecules as the active media can require working in one or more specific wavelength ranges limited by the emission wavelength range of the fluorescent dye. Fabrication processes for devices described herein can be readily established in industry for massive production. Typical processes can include, but are not limited to thin film deposition, spin coating (for polymer films), photolithography or nanoimprint (for the coupling grating in a passive plasmonic condenser).

To improve the overall performance and enable further reductions in size of a PDF microscope, a LED or OLED can be used as the active medium 130 as discussed in relation to FIG. 7B. Such integration not only eliminates the need of an external illumination light source but also significantly reduces the physical size of the plasmonic condenser 702.

Figures 8A, 8B:
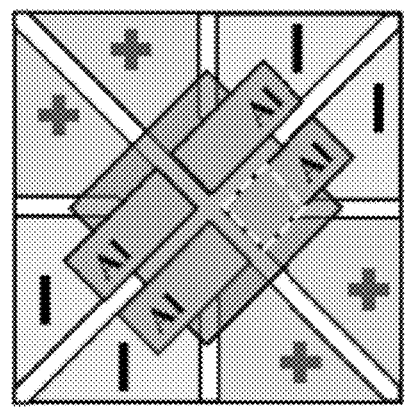
FIG. 8A and FIG. 8B show top and cross-section views illustrating features of an example of an OLED-based active plasmonic condenser.
Figure 9B:
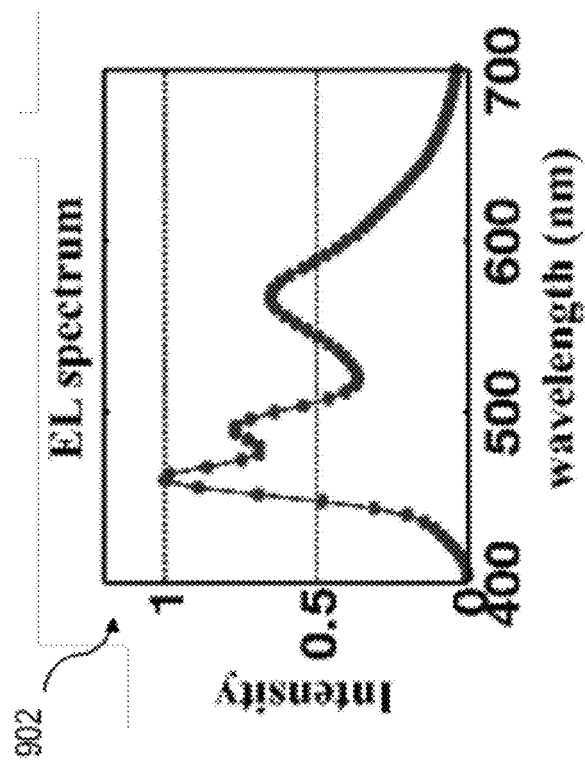
FIG. 9A and FIG. 9B show a photograph and a graph illustrating operational features of the OLED-based active plasmonic condenser in FIG. 8A and FIG. 8B.
Figure 9A:
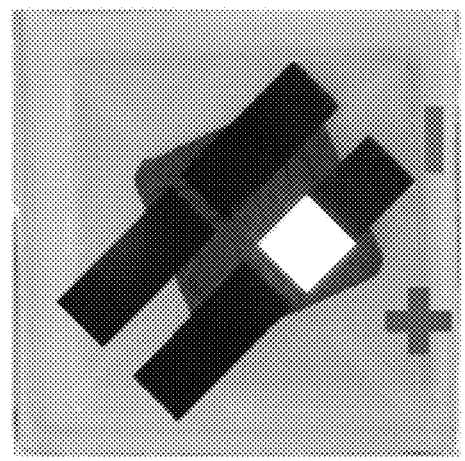

In one example illustrated in the OLED-based plasmonic condenser 800 illustrated in top view and cross-sectional view in FIG. 8A and FIG. 8B, respectively, the PC 800 can a layer of Al film deposited on top of an OLED, which can in one example include a first emission layer 802 and a second emission layer 804. Such a device can in one example be fabricated in a standard coater under a base vacuum of about $10^{-6}$ Torr. The example device illustrated in FIG. 8B can include a number of additional layers disposed in a layer stack structure around the OLED emission layers 802, 804: a 60 nm 2-TNATA film (4,4',4"-tris-[N-(2-naphthyl)-N-phenylamino]triphenylamine) 806 used for hole injection, a 10 nm non-doped NPB film (N,N'-bis-(1-naphthyl)-N,N'-diphenyl, 1,1'-biphenyl-4,4'-diamine) 810 for hole transport, a 20 nm Alq3 film (tris(8-quinolinolato)aluminium) 812 for electron transport, and a 1 nm LiF film 814 and 60 nm Al film 816 for electron injection, all of which can be supported on a appropriate support substrate, such as for a layer of example indium tin oxide (ITO) 820. When appropriate bias voltage is applied, the OLED emits white light from the ITO side, as shown in the image 900 of FIG. 9A. FIG. 9B. shows a chart 902 of a normalized electric luminance spectrum at 20 mA·cm$^{-2}$ measured by a PR650 spectrophotometer with a DC source controlled by a connecting computer.

The Al film 816 can serve as both the electrode for the OLED and as the SP supporting medium, such that SP can be excited through near field coupling with the organic light emitting molecules in the first and second emission layers. In this manner, there is no visible light emission from the Al side of the device 800, as the SP waves form an evanescent field. The choice of white light OLED enables a broadband detection across the whole visible spectrum. Note that a thin protection or passivation layer 822, for example an approximately 40 nm thick layer of NPB can also be deposited on top of the metal film 816 to isolate the organic molecules from oxygen, water, water vapor, and other potential reactants.

As a demonstration of the imaging capability of an OLED based PC 800, a single layer of two-dimensional hexagonally close packed lattice of the polystyrene beads having diameters of 2 μm was fabricated on top of the 40 nm NBP layer 822 using a self-assemble method. Since the illumination SP waves exist only at the metal surface, no alignment between the PC and the detection objective is needed, as opposed to the case of conventional transmission dark field microscopy. The scattered white light from the polystyrene particles was collected by a standard optical microscope objective (LD EC Epiplan-NEOFLUAR, 50×, NA=0.55) and then captured by an Andor camera (iXonEM 897) with 2 s exposure time, shown in FIG. 10A, FIG. 10B, FIG. 10C, and FIG. 10D, which respectively show an image 1000 obtained by OLED based PDF microscopy, a magnified image 1002 of the identified area in the image 1000, and an interpolated image 1004 of the magnified image 1002, and a noise reduction and de-convolution image 1006 of the interpolated image 1004. The observed image contrast (signal/background) enhancement is approximately 9 dB compared with a comparable bright field measurement.

As shown in FIG. 10A, FIG. 10B, FIG. 10C, and FIG. 10D, a bright signal is visible on the region between the particles with a dim signal in the middle of the particles. The area with no presence of particles expresses as an almost completely dark background. Considering the refractive indices for a polystyrene particle, the NBP layer 822, and air are 1.5, 1.8 and 1, respectively, a brighter scattering signal is obtained from where there is a larger refractive index contrast. This observation confirms that the image acquired is indeed a dark field image, which is also consistent with results obtained by fluorescent dye based PDF microscopy. Therefore, OLED based PDF microscopy is capable of forming high contrast images of objects lying close to the metal film with a highly integrated active PC without any additional light sources.

Figure 11A:
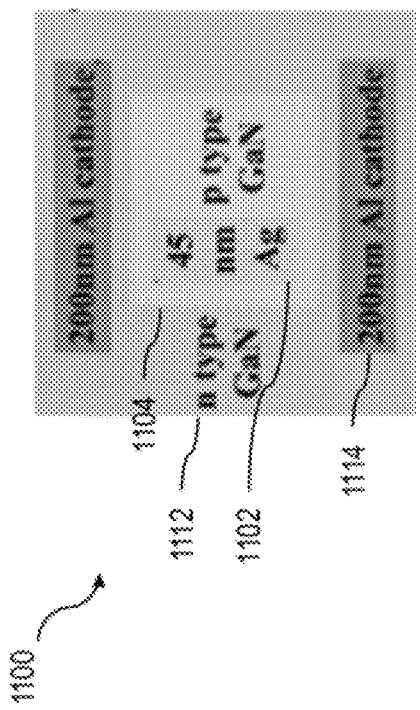
FIG. 11A and FIG. 11B show top and cross-section views illustrating features of an example of an GaN blue LED-based active plasmonic condenser.
Figure 11B:
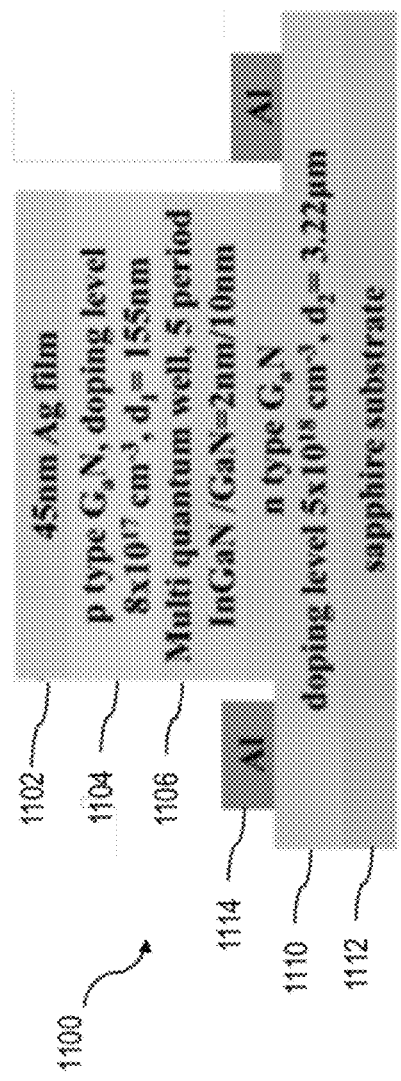

In addition to OLED-based PCs, implementations of the current subject matter also include LED-based active plasmonic condensers, such as for example a GaN blue LED-based active plasmonic condenser 1100, an example of which is illustrated in top and cross-section views in FIG. 11A and FIG. 11B. As shown in FIG. 11A and FIG. 11B, a GaN blue LED-based active plasmonic condenser 1100 can include a top metal layer 1102, which can include a silver film of approximately 45 nm thickness. The top metal layer 1102 can overlay a p type GaN LED 1104, for example having a thickness of approximately 155 nm and a doping level of approximately $8 \times 10^{17}$ cm$^{-3}$, which in turn overlays a multi-quantum well layer 1106, for example one including InGaN—GaN multiple quantum well (MQW) wafers with five periods of InGaN: (e.g. at about 2 nm thickness each) and GaN (e.g. at about 10 nm thickness each). Underlying the MQW layer 1106 can be a n type GaN layer 1110, for example with a doping level of approximately $5 \times 10^{18}$ cm$^{-3}$ and a thickness of approximately 3.22 μm. A sapphire substrate 1112 can support the entire structure, and one or more aluminum cathodes 1114 can provide contact points for the applied voltage across the LED with the top metal layer (e.g. the Ag film) 1102 serving as the anode.

A light emitting diode (LED) is a semiconductor light source. It can emit light through the electroluminescence process, in which the LED is forward biased so that electrons from the n type semiconductor are able to recombine with holes from the p type semiconductor within the p-n junction area, releasing energy in the form of photons. The color of the light, which corresponds to the energy of the photon, is determined by the band gap of the semiconductor. Modern LEDs are available across the visible, ultraviolet and infrared wavelengths, with very high brightness. They can be used in a wide range of applications.

Currently, LED is the most promising illumination source in optical microscopy. The LED light has many advantages such as diverse spectral output, wide bandwidth that is suitable for fluorescent probes excitation, and stable in terms of temporal and spatial distribution. Moreover, LED devices also have additional advantages compared with other types of light source such as tungsten-halogen or arc-discharge lamps. It is small, easy to modulate, cool when operates, more efficient than arc-discharge lamps at converting electricity into visible light. It also has extremely long lifetime and can instantly illuminate at full intensity. Recently, as the LED fabrication technique improves, the available high-performance LEDs are sufficiently bright to function individually as a highly effective light source for optical microscope.

Figure 12C:
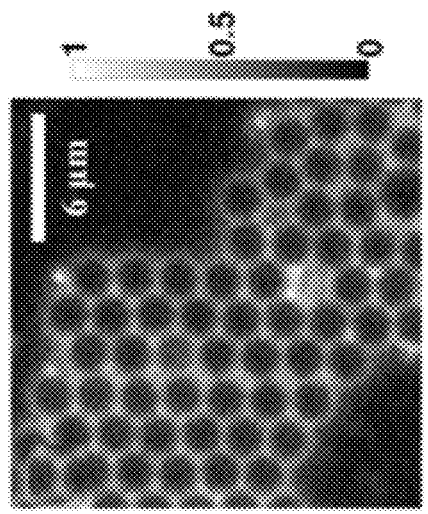
FIG. 12A, FIG. 12B, and FIG. 12C respectively show a photo of the device in FIG. 11A and FIG. 11B, a graph of the device's current-voltage curve, and a dark field image of self-assembled polystyrene particles (diameter ~2 μm) formed by LED based PDF microscopy.
Figure 12A:
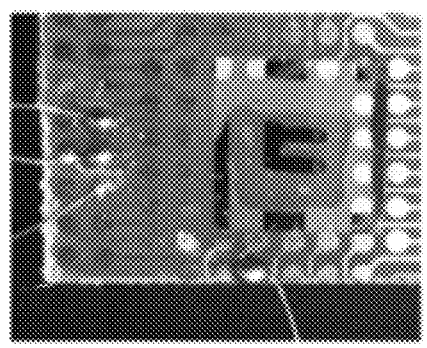
Figure 12B:
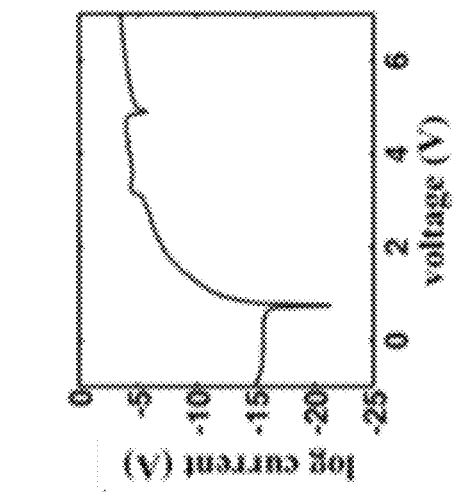

FIG. 12A, FIG. 12B, and FIG. 12C respectively show a photo 1200 of the device in FIG. 11A and FIG. 11B, a graph 1202 of the device's current-voltage curve, and a dark field image 1204 of self-assembled polystyrene particles (diameter ~2 μm) formed by LED-based PDF microscopy collected by a standard objective (NOT a dark-field objective) from Carl Zeiss (LD EC Epiplan-Neofluar 50× NA=0.55).

The following describes an experimental demonstration of the proposed PDF microscopy. For simplicity of explanation, an active plasmonic condenser is described as shown in FIG. 7A. The plasmonic condenser fabrication started with spin coating a 150 nm thick polymethyl methacrylate (PMMA) film on a cover glass substrate. The PMMA was mixed with Rhodamine 6G molecules with concentration around $10^{-4}$ M. After a 2 minutes soft bake process, a 60 nm thick silver film was deposited on top using e-beam evaporation method. A water droplet comprising 2 μm sized (diameter) polystyrene beads dropped on top of the silver layer. The water was self-evaporated and the polystyrene beads were left with certain self-assembled patterns. The polystyrene beads were used as test objects.

Various testing and experiments have been performed on devices having one or more feature consistent with implementations of the current subject matter. For example, a fabricated fluorescent active PC was tested using aggregations of about 2-μm sized (diameter) polystyrene beads. A two dimensional (2D) hexagonally close packed lattice of the polystyrene beads was fabricated on top of silver film using the self-assembly method. The sample was first examined by using a standard optical microscope dark field objective (e.g., an EC Epiplan-Neofluar, 50×, NA=0.8). The reflection mode dark field image is shown in the image 1300 shown in FIG. 13A with a green filter (560±10 nm band pass) added in the light path. As a comparison, the same sample was examined using PDF microscopy and to generate the image 1302 shown in FIG. 13B. The same objective was used for both techniques. However, in the PDF microscopy image, a pair of band pass filters were used for the excitation (530±10 nm) and detection light (560±10 nm), respectively, based on the properties of the dye in the active media layer. It can be seen from a comparison of the images 1300 and 1302 in FIG. 13A and FIG. 13B that the contrast of the image obtained using the PDF microscopy approach is significantly improved relative to the image obtained using conventional DF microscopy, especially the contrast between the center parts and the interspaces of the polystyrene, as marked by the arrows.

The dark field module for common dark field microscopy was not used in the PDF microscopy. In other words, there is no specific need of module or objective for the PDF microscopy; any objective can do the job. As would be expected, the PDF microscopy image shows superior contrast with simplified configurations. The resolution, as marked by the red arrows in FIG. 13A and FIG. 13B, is also remarkably improved. The resolution can be significantly improved by a better design of the plasmonic structure in the PDF microscopy.

Figure 14A:
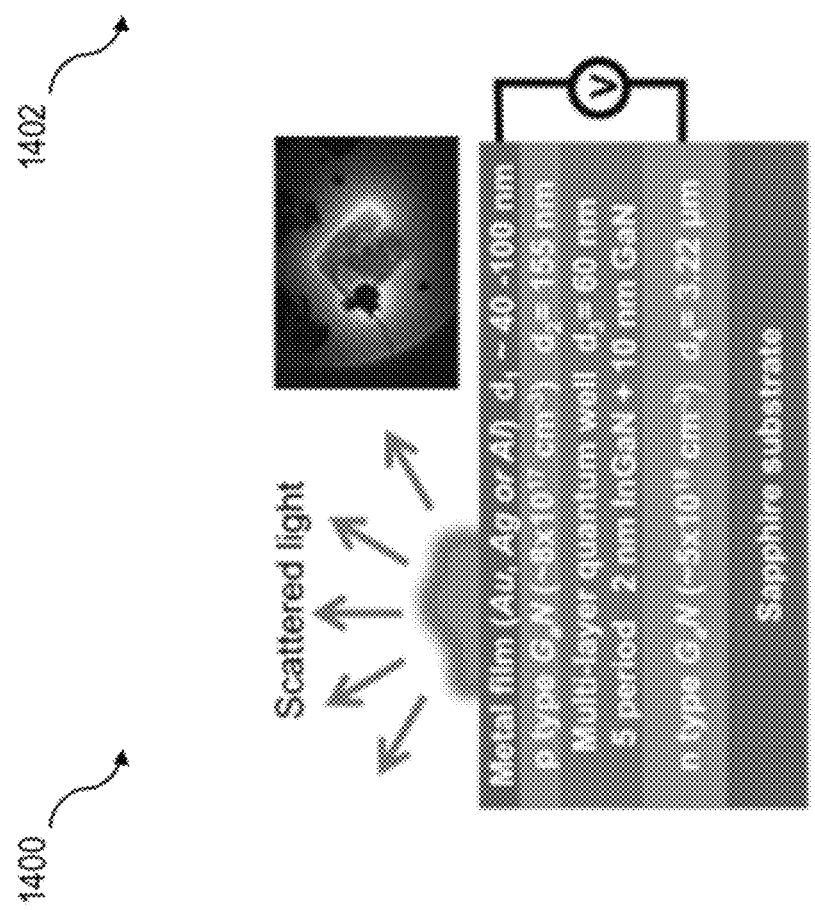
FIG. 14A and FIG. 14B show a schematic example of a structure of a LED-based based PC and a dark field image of self-assembled polystyrene particles (diameter ~2 m) acquired using a conventional objective and the LED-based based PC.
Figure 14B:
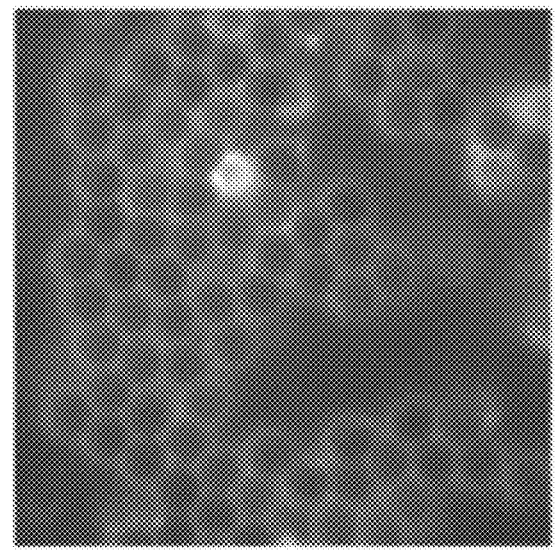
Figure 15A:
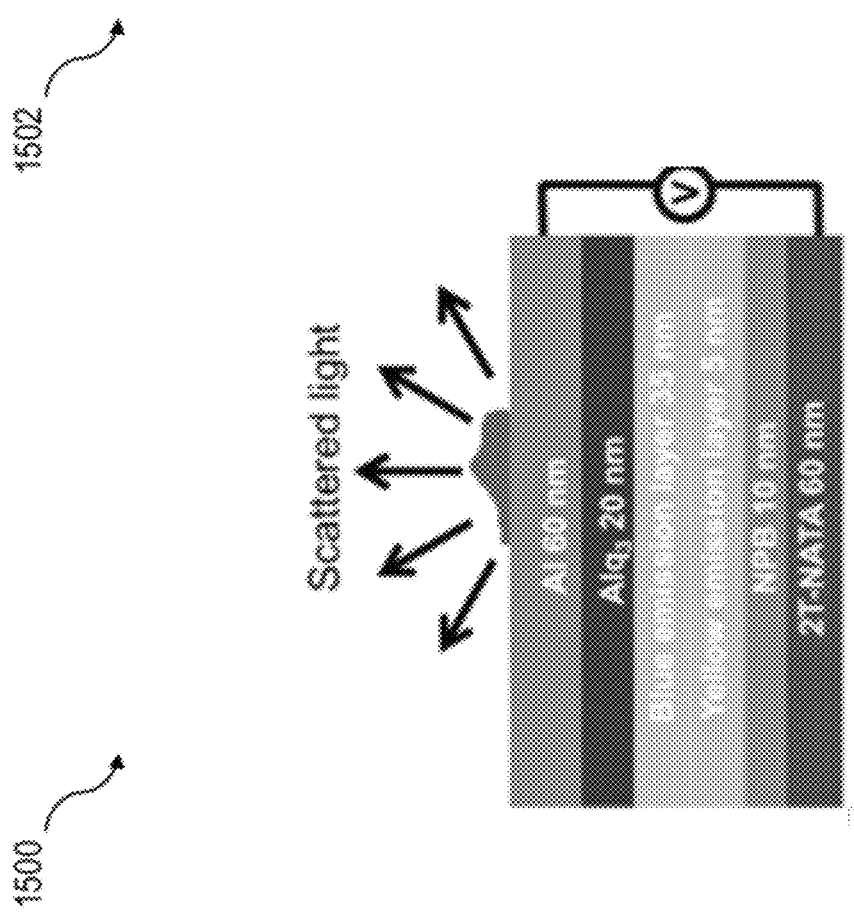
FIG. 15A and FIG. 15B show a schematic example of a structure of an OLED-based PC and a dark field image of self-assembled polystyrene particles (diameter ~2 m) acquired using a conventional objective and the OLED-based based PC.
Figure 15B:
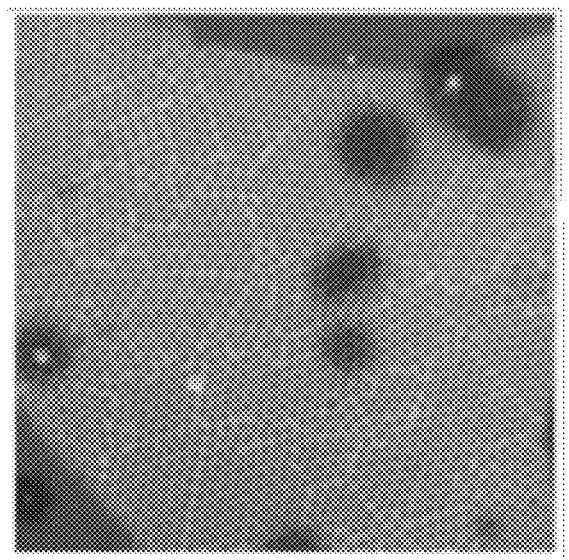

LED-based and the OLED-based PC design were also tested by depositing a layer of metal film on top of the LED and OLED structure and measuring the corresponding dark field images of self-assembled polystyrene particles (diameter ~2 µm). The metal film serves as both the electrode of the LED/OLED and the supporting media for SPs. FIG. 14A and FIG. 15A respectively show the schematic structures 1400, 1500 of a GaN blue LED based PC and an white light OLED based PC. FIG. 14B and FIG. 15B show corresponding dark field images 1402, 1502 measured by a standard objective from Carl Zeiss (EC Epiplan-Neofluar, 50×, NA=0.8). For FIG. 14B, an additional four times magnification was added between the microscope and the CCD camera to show the detailed image. The background in these dark field images comes from the direct transmission of the LED or OLED light through the metal film and can be significantly decreased by optimizing the plasmonic structure.

Figure 16B:
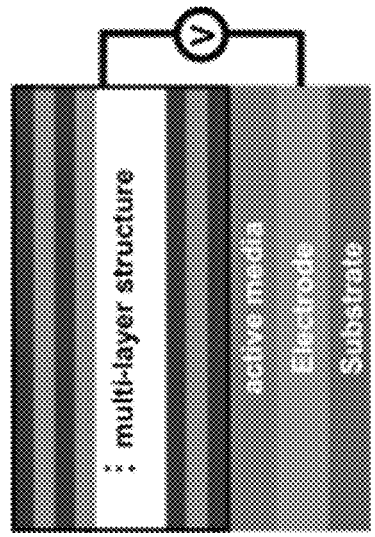
FIG. 16A and FIG. 16B respectively show schematic examples of structures of an LED-based PC for use with fluorescence microscopy and an active PC with multi-layer structure as the supporting materials for the SP.
Figure 16A:
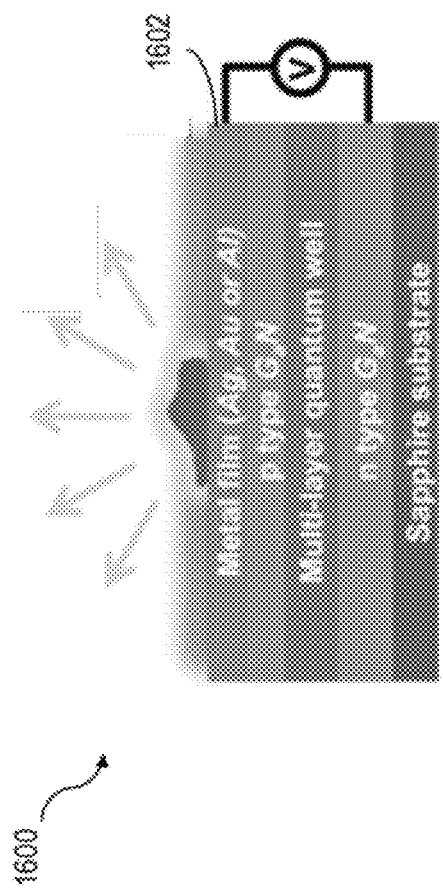

Besides generating dark field images, a PC consistent with implementations of the current subject matter can also form fluorescent images when one or more objects labeled with fluorescent dyes are within in the SP evanescent field region, as is shown in the cross-sectional diagram 1600 of FIG. 16A. Due to the short penetration depth of a SP field, the PC 1600 is capable of reducing the fluorescent signals from the areas far from the metal film 1602. Therefore, this approach using a PC can achieve the same image quality as TIRF with much more compact and low-cost PCs. Moreover, a metal/dielectric multi-layer structure can also be used to generate SPs, as shown in the shown in the cross-sectional diagram 1604 of FIG. 16B. Compared with a pure metal film (such as Au, Ag and Al film), a metal/dielectric structure can support SPs with larger wave vectors and greatly reduce the direct transmission of light through the structure. Additional detail on the use of meta-materials to affect the decay distance of the coupled radiation emitted into the far field from a PC is provided below.

As shown above, the PDF has been experimentally demonstrated for high contrast imaging. The image quality of the PDF microscopy is strongly related to the near field coupling between the active medium and the SPs on the metal film in the PC, which has been intensively investigated. A model may be used to study the coupling between a dipole in the vicinity of a metallic interface, as the fluorescent dyes can be modeled as dipoles with isotropic orientations. When the thickness of the silver film is about 60 nm, about 40% of the energy can be transferred to SPs. The remaining 60% of the light will be decayed by the about 60-nm silver layer, resulting in very low transmission. So in the far field only the scattered SPs by the objects can be detected. The surface roughness, in addition to the object, can also scatter the SPs into free space photons thus contributing to the background. In one advantageous implementation of a PC, the surface roughness is less than about 2 nm in terms of root mean square (RMS), although other RMS values may be possible. The scattered light from the random roughness of such a smooth interface is very weak, resulting in the high contrast for example as shown in FIG. 13B, FIG. 14B, FIG. 15B, and in other experimental results described in this document and/or illustrated in the associated figures.

Because the high contrast imaging capability of a LED-based or an OLED-based PC originates from the evanescent nature of the SPs, the resolution along the direction perpendicular to the metal film as well as the signal to noise (S/N) ratio strongly depend on the decay property of the SPs. Due to its short decay length, unwanted scattering from objects far from the interface can be avoided and only objects within close vicinity to the plasmonic structure are imaged. Further increasing the z resolution and the S/N ratio can be realized by engineering the SP decay properties, for example consistent with additional implementations discussed in greater detail below. Using carefully designed plasmonic structures, the SP field can be caused to have a decay length much shorter than that created by other techniques such as total internal reflection.

Besides the SP decay length along the optical axis above the evanescent wave surface, the S/N ratio can also be influenced by other factors such as the coupling efficiency to SP and the surface roughness of the films. The near field coupling between the organic light emitting molecules and the plasmonic structure can be calculated by modeling the device as isotropically orientated dipoles in the vicinity of a metallic structure. For a LED-based or an OLED-based device such as those described above, about 50% of the energy can be coupled to SP for light wavelengths in a range of about 400 nm to 700 nm. The remaining energy is either coupled to lossy waves, emitted from the ITO side of the OLED or attenuated by the 60 nm Aluminum film, thus resulting in less than 0.01% of the energy transmitting to objects side and contributing to the background signal as shown in the graphs 1700 and 1702 in FIG. 17A and FIG. 17B.

Therefore, light generated through the scattering of the evanescent field by objects are orders of magnitude stronger than the direct transmission background. Such high contrast can be further increased by various PC optimization processes such as increasing the SP coupling efficiency. Besides the direct transmitted light through Al film, photons rising from the scattering of the SP by surface roughness also contribute to the background. For this device, the root mean square (RMS) surface roughness is about 2 nm and can be further reduced by use of optimized film deposition techniques. The 2 s exposure time in this demonstration was used to obtain high S/N ratio. The image acquisition time can be reduced for real-time microscopy applications, combined with other methods such as increasing OLED power and using higher electronic gain for imaging CCD detector.

As noted above, it is possible consistent with further implementations of the current subject matter to improve upon the performance of both SP-based microscopy and TIRF-based microscopy by modifying the decay length (d) of the induced evanescent waves. The most commonly available NA of a TIRF objective lens is above 1.40 while 1.65 is the highest available NA. These values correspond to minimum decay lengths (or Z-resolution) of around 80 and 40 nm, respectively. Additionally, high NA objectives are typically highly sensitive to alignment and thus must be accurately positioned and aligned to assure the total internal reflection generation. Thus the conventional TIRF microscopy is instrumentally complex, costly, bulky, and mostly importantly, with the highly limited Z-resolution (most commonly around 80~100 nm).

Consistent with additional implementations of the current subject matter, a new type of optical section biological imaging technique, referred to herein as chip-scale integrated meta-materials-mediated evanescent wave (MMEW) microscopy, can be applied to achieve multimode (both dark-field and fluorescence) imaging capability with a minimum Z-resolution (or axial resolution) well beyond the limit (approximately 40 nm) that can generally be obtained using conventional total internal reflection fluorescence (TIRF) microscopy techniques. IN some implementations, MMEW microscopy can synergize the unique optical tunability of multilayer meta-materials, the evanescent wave nature of surface plasmon, and the sensitivity and selectivity of fluorescent probes to provide substantially improved performance for optical section microscopy among other possible applications.

Figure 18:
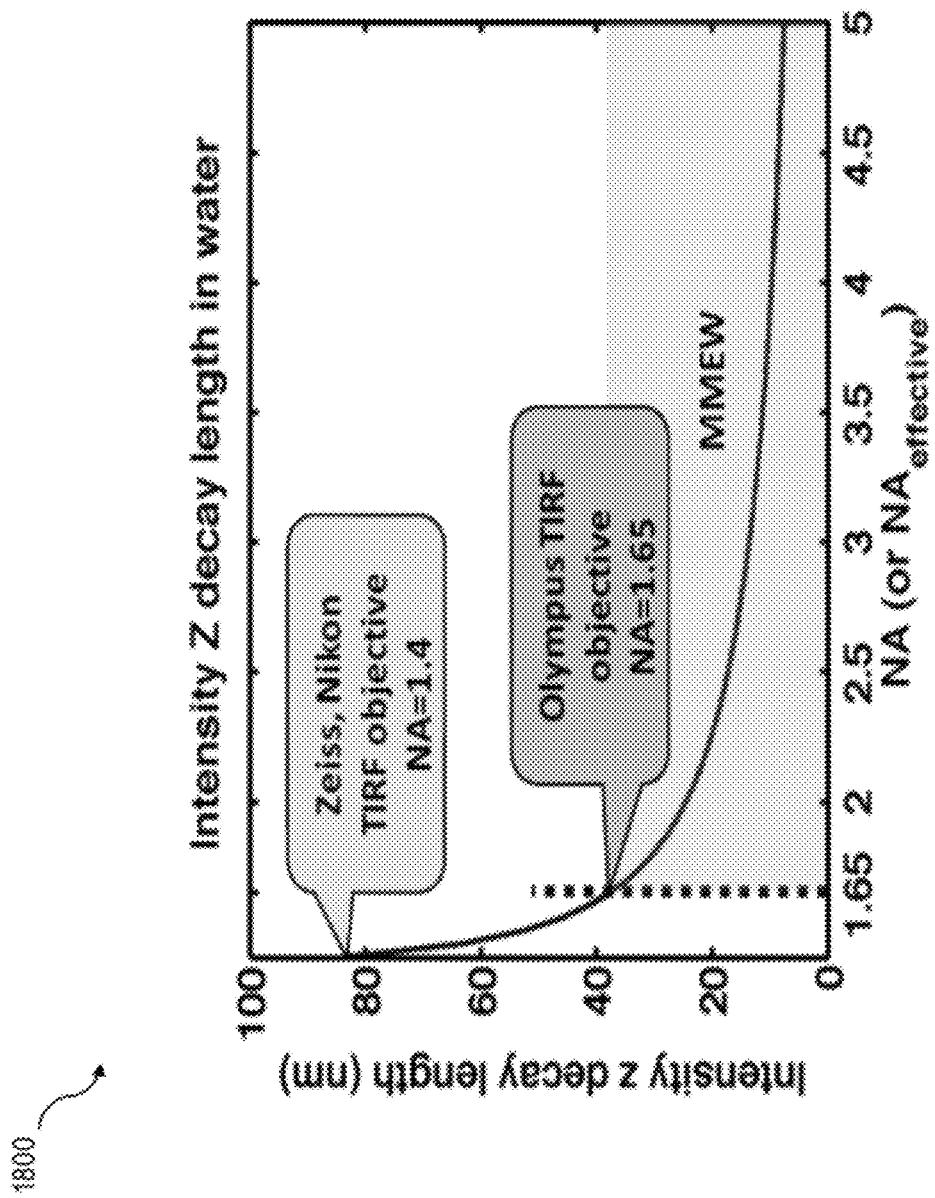
FIG. 18 shows a graph illustrating a comparison of the intensity decay length (or Z-resolution) between conventional TIRF microscopy (1.4 is the most common NA; 1.65 is the highest NA available) and meta-materials-mediated evanescent wave (MMEW) microscopy with an effective NA greater than 1.65.

TIRF microscopy as currently applied generally uses total internal reflection to generate EWs. As such, the numerical aperture (NA) of the objective (see equation 5 above) can determine the minimum Z-resolution of a TIRF approach as described by the EW decay length (d) as shown in the chart 1800 of FIG. 18, which shows a comparison of the intensity decay length (or Z-resolution) between conventional TIRF microscopy (1.4 is a common NA, while approximately 1.65 is the highest NA available) and meta-materials-mediated evanescent wave (MMEW) microscopy with the effective NA more than 1.65. This lower limit on the minimum Z-resolution not only reduces the contrast and sensitivity of TIRF microscopy due to excited fluorophores in the inner part of cells, but can also significantly limit the utility of TIRF-based approaches for optical section and surface imaging, especially for biological systems with feature dimensions of interest that are substantially smaller than 40 nm (e.g. cell membranes of approximately 5-10 nm).

Figure 19:
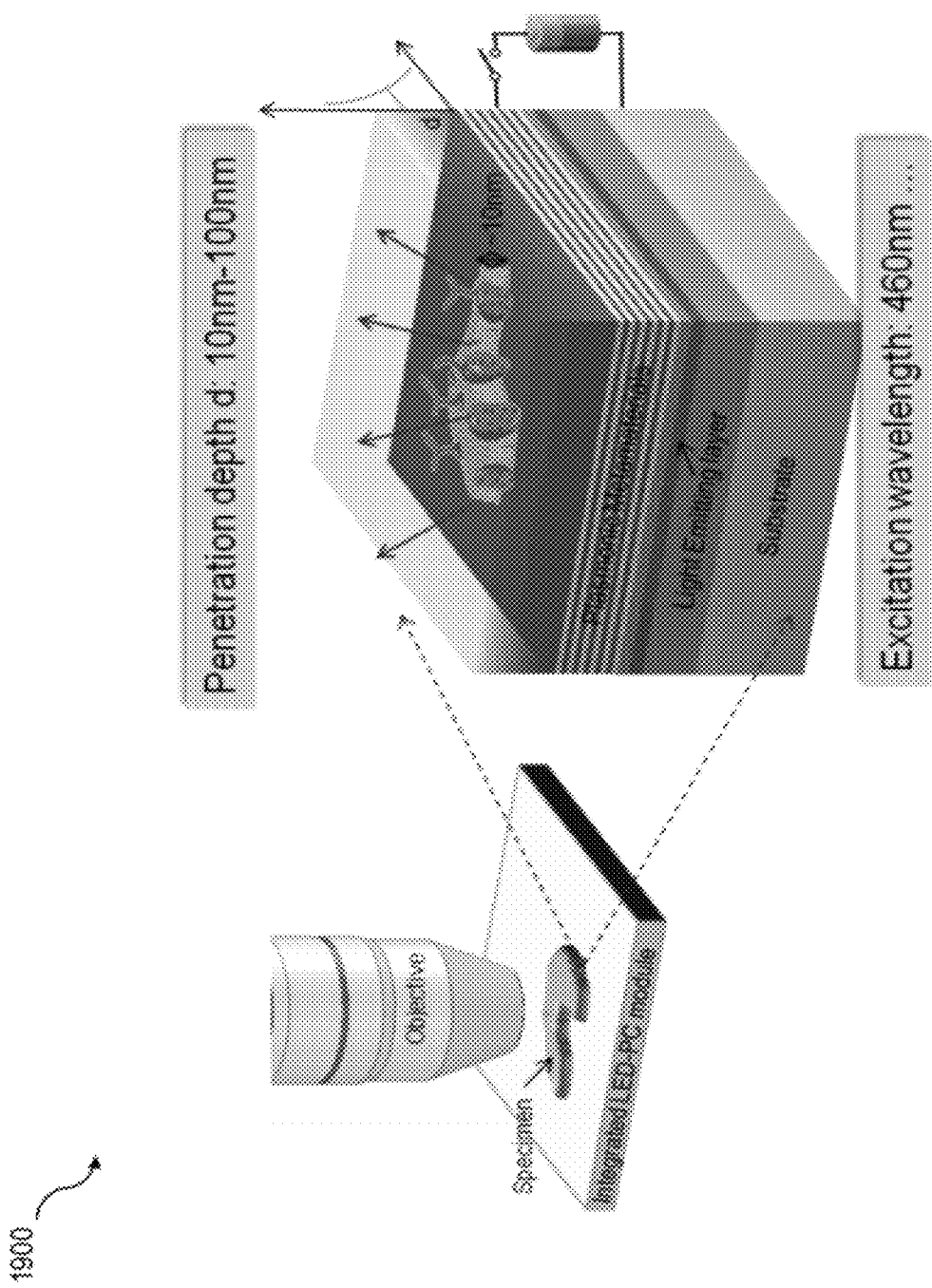
FIG. 19 is a diagram showing features of a LED-based chip-scale integrated meta-materials-mediated evanescent wave (MMEW) microscopy approach.

Some implementations of the current subject matter can provide, among other possible advantages, benefits, or the like, imaging of biological materials and/or other materials with very thin (e.g. nano scale) feature thickness using chip-scale integrated meta-materials mediated evanescent wave microscopy (MMEW) techniques to achieve low-cost, compact, and controlled super Z-resolution imaging. As shown in the schematic diagram 1900 of FIG. 19, implementations consistent with the current subject matter can integrate multilayer meta-materials with a light source such as light emitting diode (LED) to replace a bulky and expensive glass lens-based TIRF illumination system. This integrated structure can use the near-field of the emitted light, instead of total internal reflection, to induce surface plasmons (SPs), for example as discussed in regards to the implementations described elsewhere herein. The SP evanescent waves can excite fluorophores or scatter lights for far-field imaging. The excited SPs can have much larger in plane wave vectors than those of the evanescent field generated in TIRF microscopy, which can lead to significantly higher resulting Z-resolution (for example, smaller than 10 nm) as shown in FIG. 19.

A multilayer, meta-materials-based plasmonic condenser (PC) can be part of a light source integrated PC plasmonic meta-materials illuminator (PMI) consistent with one of more implementations of the current subject matter. Besides the improvement in Z-resolution noted above, a PMI similar to the examples described herein, which can serve as a core component of a MEWM, can provide other advantages relative to a conventional illumination system. For example, a PMI can be highly integrated and can be fabricated on a large scale with correspondingly reduced costs per unit, thereby substantially reducing the cost of a MEWM relative to other light source approaches. Because the PMI can be considered as an integrated version of light source and condenser, energy can be more efficiently used relative to the energy wasted by the light stop in a conventional TIRF microscopy configuration for dark-field microscopy. Finally, the PMI controls the light propagation direction along the surface automatically, which can eliminate the need for alignment of the lighting source and the objective lens, thereby improving ease o use of a microscopy approach incorporating such features.

Because SPs always have larger wave vectors than that of the corresponding light at the same frequency, SPs need to be excited with a coupling mechanism, such as with a prism or grating. There are two configurations which are well known to excite SPs using a prism; the Otto and the Kretschmann setups. In the Otto setup, evanescent wave is used to excite SPs on a thin metal (for example gold) film. In the Kretschmann configuration, evanescent waves penetrate through a metal film and excite SPs at the outer side of the film. A grating can also be used to bridge the momentum gap between photon and SP through grating diffraction $k_{out}=k_{in}+2\pi/\Lambda$, with $\Lambda$ being the period of the grating. According to the dipole model, when a light emitting particle is in close proximity of a metal film, SP modes may also be excited by the near field of the dipole. The light emitting medium may be any type of luminescent material, but the emitter must be within the near-field distance from the metal thin film to realize the coupling with SP modes. The smaller the distance is, the larger wave vector of the SP modes the near-field light can support. SP modes may also be excited directly by electrons, such as metal-insulator-metal tunneling junction.

A PMI consistent with implementations of the current subject matter can include an active medium that can excite SPs through the near-field coupling as mentioned previously. For example, as shown in the diagram 2000 of FIG. 20A, a dye-based active medium can be used. In principle, the active medium may include any material that is able to generate either coherent or incoherent light sources. Examples include fluorescent molecules, ion doped crystal or glass, quantum dots, semiconductor quantum wells in the LED, and etc. Because of the various advantages of LED mentioned above, an LED-based PMI chip 2002 as shown in FIG. 20B can advantageously combine a conventional LEDs with appropriately designed plasmonic multilayer meta-materials structures to achieve controlled super Z-resolution far-field imaging, while making PMI extremely compact. Although the signal-layer metal film can enhance the LED performance through the quantum well (QW)-SP coupling, the decay length of the resulting evanescent field on the sample side is very similar to that without the metal film. Therefore, the Z-resolution can be significantly improved by replacing a single metal film with a multilayer plasmonic meta-material structure. Due to the near field coupling, more SP modes with large wave vectors appear in the multilayer structure, leading to the reduced decay lengths (or higher Z-resolution compared with the case of a single layer). In addition, compared to the case of a single layer metallic structure, the meta-materials possess a few more design freedoms such as the refractive index and the thickness of the dielectric layer. It is therefore possible to control the decay length by tuning the intricate coupling between various metallic layers.

Efficient QW-SP coupling to the whole multilayer stack is advantageous for achieving performance improvements. However, the whole multilayer stack need not be placed into the near field of the QW. Such a configuration can be quite challenging to realize in practice when the stack becomes thick. In fact, the only requirement of an efficient coupling of an QW and the associated meta-materials is that the very first few metallic layers of the meta-material have to be in the near field of the QW. The SPs in the first few layers can be coupled into the rest of the metal films through a SP-SP coupling mechanism as shown in an exemplary simulation illustrated in the graph 2004 of FIG. 20C. Clearly, the topmost layer of metal is quite far away from the dipole but the SPs in those layers still can be efficiently excited through SP-SP coupling.

In addition, to achieve the far-field imaging, the excited SPs need to interact with the samples of interest to generate the far-field radiation light either by scattering or exciting the fluorescence at the interface of the sample side by the near-field coupling. This coupling is the same as the coupling between QW and meta-materials and thus can also be model as the coupling between a dipole in the vicinity of a metallic interface. For example, as shown in FIG. 6A, FIG. 6B, and FIG. 6C discussed above, the energy transfer from the excited fluorescent molecules to the adjacent metal film depends on the distance between them. For a very short distance, usually less than approximately 10 nm, fluorescent molecules are almost complete quenched because most fluorescent energy is transferred to electron-hole pairs in the metal (excitons) and finally dissipated as heat through near field resonant dipole-dipole interaction (e.g. as a Forster transfer). For intermediate distance (e.g. approximately 10-200 nm), the fluorescent energy can be partially coupled to the SPs in the metal film while partially radiating out. Considering the setup in FIG. B, the radiated waves are intended light because it forms the far-field image.

For these reasons, it can be advantageous for LED-based multilayer PMI chips to include multilayer metaimaterials designed to decrease the decay lengths of excited SPs. The optimization parameters for such arrangement can include the selection of composite materials, the layer number, and the thickness for each layer. In addition, the last layer can be set to be the dielectric layer with thickness around 10 nm to minimize the fluorescence quenching. The structure between the LED and the multilayer meta-materials can also be designed to enhance the QW-SP coupling and generate the desired multilayer modes effectively by e.g. adjusting the thickness of the top p-GaN layer.

A GaN based blue LED can in some illustrative examples be fabricated in some examples using metal-organic chemical vapor deposition (MOCVD). FIG. 21A and FIG. 21B show an example of a layered structure 2100 of a typical GaN LED and a graph 2102 of its emission spectrum, respectively. InGaN—GaN multiple quantum well (MQW) wafers can optionally be grown on n-GaN by MOCVD. The example structure can include a n-GaN (3.22 μm) layer, 5 periods of QWs (InGaN: 2 nm, GaN: 10 nm), followed by a p-GaN layer (100 nm). The doping concentration for n-GaN and p-GaN can be ~$5 \times 10^{18}$ cm$^{-3}$ and ~$8 \times 10^{17}$ cm$^{-3}$, respectively. This growth process can be very reliable and can routinely grow GaN based LEDs with various QW numbers as well as desired thickness of the p-GaN cap layer. Further optimization processes can achieve higher carrier concentrations for both p-type and n-type semiconductors as needed.

Fabrication of multilayer meta-materials such as those described herein in relation to the disclosed implementations can be accomplished using thin film deposition, for example by e-beam evaporation, sputtering, or the like. The quality of the multilayer meta-materials can be characterized using a variety of techniques, including but not limited to cross-sectional SEM imaging, and an optical spectrum method in which transmission spectra based on both real structure and effective medium theory can be calculated and compared to the measurement data. The transmission peak location and the bandwidth are the two major parameters to identify the quality of the multilayer samples.

Figure 22B:
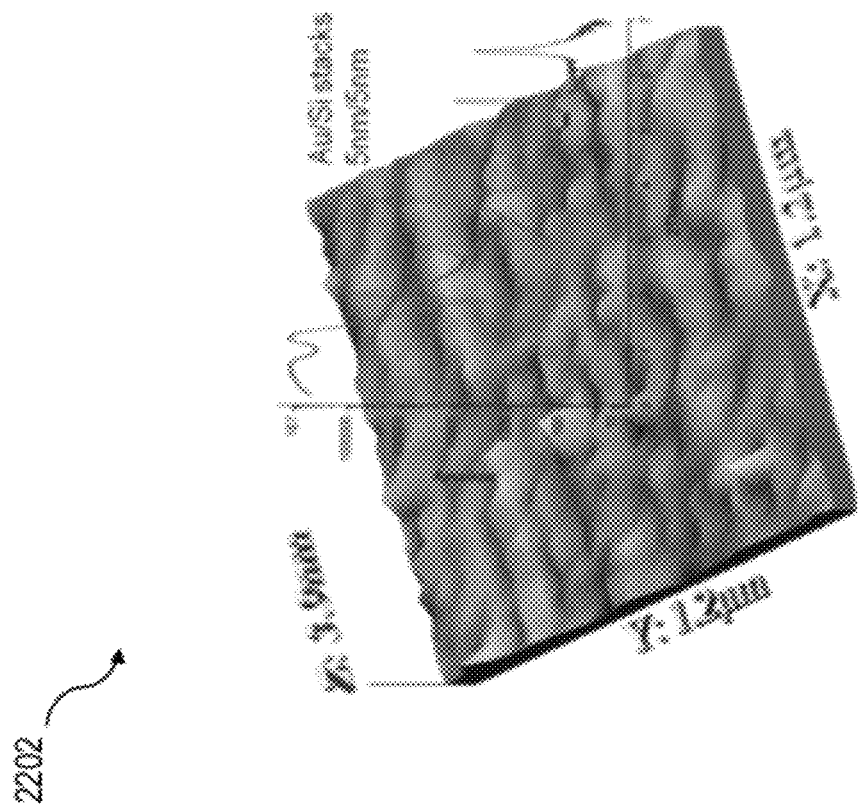
FIG. 22A and FIG. 22B respectively show a TEM image of a multilayer (Ag/Si) plasmonic meta-material fabricated by DC magnetron sputtering with a thickness of each layer of approximately 10 nm and a total thickness of the stack of approximately 1 μm and an AFM mapping of the Au/Si multilayer surface on the top-most layer showing surface roughness (RMS) on the scale of 3 Å.
Figure 22A:
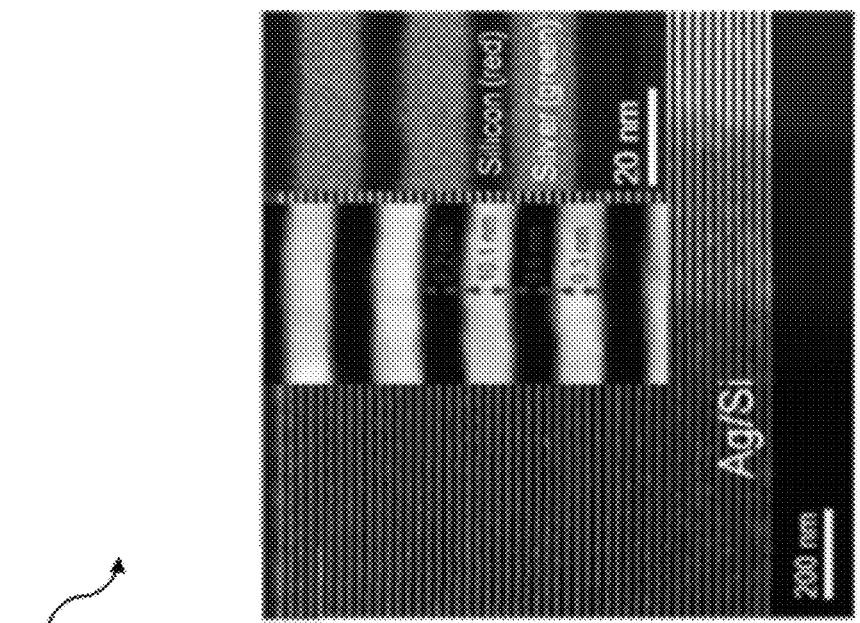

Deposition of the various layers required for a sub-30 nm scale multilayer meta-material device can optionally be carried out using a multi-gun high vacuum level sputtering system. Ag/Si multilayers can in some illustrative examples be deposited at a scale of approximately 10 nm, for example as shown in the TEM image 2200 of FIG. 22A. Ag/Si and Au/Si multilayer samples with thickness scales of approximately 5 nm for each layer can in some illustrative examples be obtained by DC sputtering Ag/Au and Si at very slow rate (1.6 and 0.16 Å/s, respectively). FIG. 22B shows a graph 2202 illustrating an example of X-ray reflectivity measurement for such a multi-layer structure illustrating the Brag reflection peaks for the periodic lattice. The X-ray reflectivity measurement of such a Au/Si superlattice sample clearly shows the periodic nature of the stack (inset in FIG. 22B). The stack comprises 30 pairs of Au/Si films and the thickness for each Au and Si layer is 5 nm. In the example shown in FIG. 22A and FIG. 22B, the surface roughness is about 3 Å. For fabrication of even thinner layers, for example on the scale of about 1-2 nm per layer, the quantum-size effect of the electrons can play a significant role, such that classical meta-material treatments and properties may require correction based on quantum mechanical calculations.

To achieve various effective permittivities at desired frequencies, an appropriate metal/dielectric combination is critical. Multilayer combinations that can be used in conjunction with implementations of the current subject matter can include, but are not limited to Ag/Si, Au/Si, and Ag/Al$_2$O$_3$ as well as other multilayers involving Al, Au, Al$_2$O$_3$, SiO$_2$, and TiO$_2$. Multilayer samples can be fabricated on glass, sapphire, silicon wafers, GaN substrates, and the like with various material combinations as well as different filling ratios.

Verification of evanescent field generation through near field coupling between a light source (such as quantum wells in LED) and the multilayer structure has been performed using LED-based PMI chips. A diagram 2300 of the structure and graph 2302 showing an emission spectrum of a GaN blue LED are shown in FIG. 23A and FIG. 23B, respectively. In order to achieve super Z-resolution, the multilayer meta-materials tested were designed so that the decay length of the evanescent field generated at the multilayer/air interface is about 20 nm, as confirmed by numerical simulation shown in the graph 2302 of FIG. 23B. The multilayer, which consists of five periods of 30 nm Ag and 40 nm Al$_2$O$_3$ with the last layer of Al$_2$O$_3$ 10 nm, acts as both the evanescent field supporting media and the electrode of the LED. The test samples were self-assembled 200 nm (diameter) polystyrene beads at top of the multilayer film. The sample was first examined using a standard dark field objective (Long working distance 50×, NA=0.5) with the image 2304 shown in FIG. 23C. As a comparison, the same sample was examined using MMEW microscopy with the image 2306 shown in FIG. 23D. Note that the light scattered by the beads was collected by the same objective for both techniques. Different from conventional dark field microscopy, the illumination light of the MMEW microscopy only exists on the top surface of the PMI in the form of SPs. The depth of field and thus the sensitivity of the MMEW microscopy along the Z-direction are solely determined by the decay property of the SPs. As a natural consequence, the images of the two techniques reflect very different information of the object. FIG. 23D shows the bottom image of the self-assembled polystyrene beads while FIG. 23C shows the top image 2304. Moreover, because SPs are automatically generated through the near-field coupling with quantum wells, incident angle control or alignment is not needed.

Figures 24A, 24B:
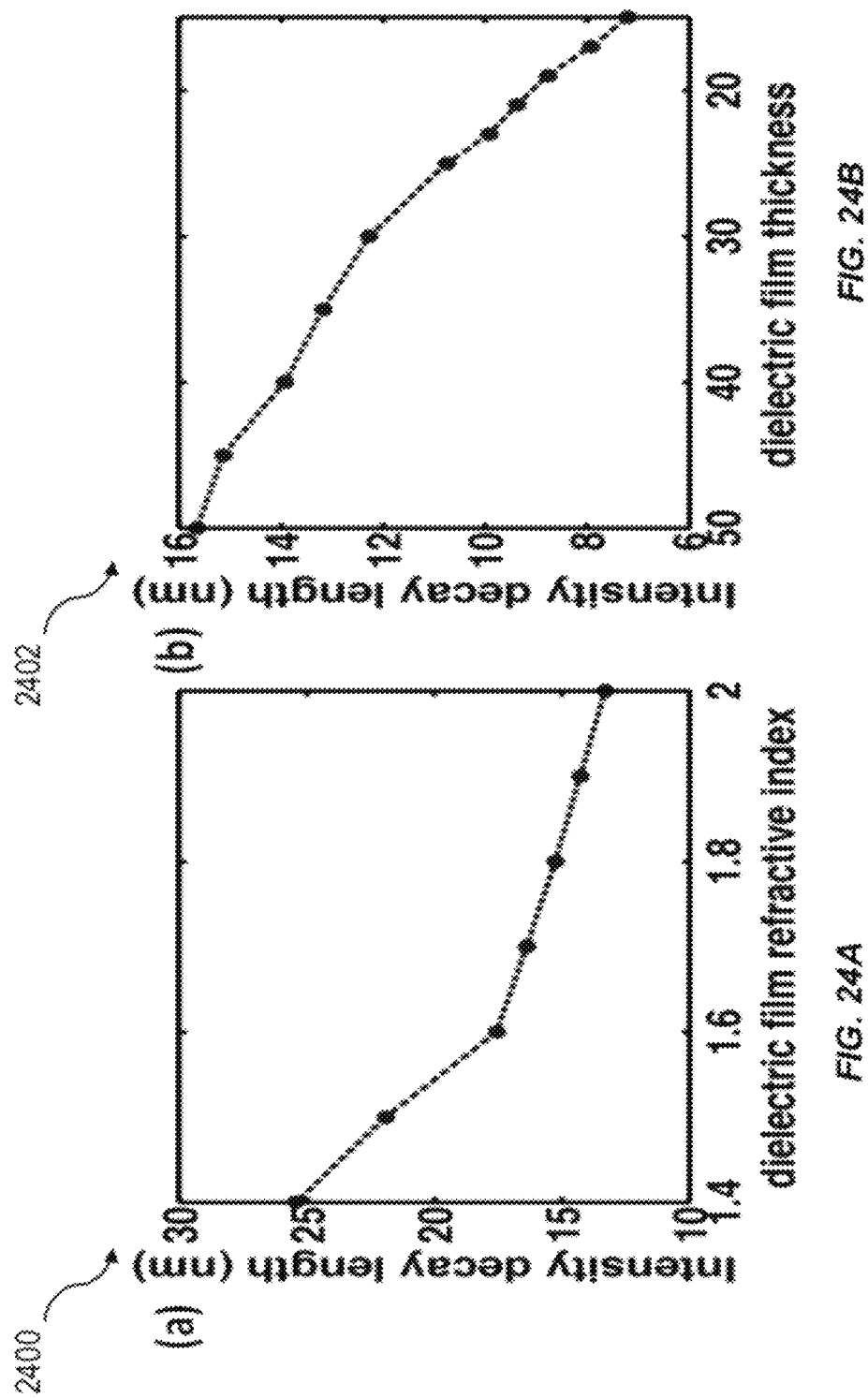
FIG. 24A and FIG. 24B are graphs respectively showing an intensity decay length dependence on the refractive index of a dielectric film at 460 nm in water for a multilayer composed of 20 periods of 30 nm Ag/50 nm dielectric films and an intensity decay length dependence on the dielectric film thickness of a dielectric film at 460 nm in water for a multilayer composed of 20 periods of Ag/Al$_2$O$_3$ films with a thickness of Ag film fixed at 30 nm.

The Z-resolution (or d) limit, which is determined by plasmonic metamaterials structure design, however, has to be studied in more details. Similar to equation 3 above, which describes d for conventional TIRF microscopy, the d for MMEW microscopy can be written as $$d = \frac{1}{2k_z} = \frac{\lambda_0}{4\pi\sqrt{NA_{eff}^2 - n_2^2}}, NA_{eff} \equiv \frac{k_{sp}}{k_0} \quad (6)$$

where $n_2$ is the refraction index of the media at the sample side where the evanescent field is generated, $k_{sp}$ is the wave vector of the excited SP mode of the multilayer metamaterials, $k_0$ is the wave vector of the free space LED light, and $NA_{eff}$ is called the effective NA of the metamaterials. As indicated in equation 6, the maximum effective NA for PMI, thus the minimum Z-resolution, is determined by $k_{sp}$ for a chosen LED. In principle, the SP wavevector for a single metallic layer can be designed to reach a very high value by selecting appropriate materials, metal layer thicknesses, and working wavelengths. In addition, the single layer of metal film can also be replaced by a composite material that includes much thinner metal/dielectric multilayer structures for more opportunities to engineer the SP modes. For a fixed metal film thickness and period, the d decrease with the increase of the refractive index of the dielectric layer or the decrease of the thickness of the dielectric film, as shown in the graphs 2400 and 2402 of FIG. 24A and FIG. 24B, respectively. This indicates that thickness and refractive index of the dielectric film have significant influence on the decay length.

Beside these two factors, the thickness of metal film and the number of period can influence the wave vector range that is supported by the multilayer structures. As the metal film thickness or the number of period increases, the range becomes smaller, which can result better decay length control. By taking into account one or more of the aforementioned factors, a plasmonic meta-material structure for MMEW microscopy can be designed and optimized to achieve Z-resolutions even further beyond those obtainable by TIRF microscopy.

The multilayer metamaterial is deposited on top of a p-type GaN/MQW structure (FIG. BA and FIG. GA), and the thickness of that p-type GaN spacer layer can be critical for the QW-SP coupling. Two parameters that can directly affect the selection of the thickness of the p-GaN layer include the SP penetration depth (L) of the SP fringing field into the semiconductor and the depletion width (D) of the p-side in the p-n junction. Generally, the p-GaN layer should be thinner than L to obtain strong SP-QW coupling. In the case of a single metal film, L is give by $$L = \lambda/2\pi\sqrt{(\varepsilon'_{GaN} - \varepsilon'_{metal})/\varepsilon'_{GaN}^2}, \quad (7)$$

where $\varepsilon'_{GaN}$ and $\varepsilon'_{metal}$ represent the real part of the permittivity of the semiconductor and metal. L is estimated to be 42 nm if the working wavelength is at 460 nm. The thickness of the p-GaN layer should be larger than D to maintain the p-n junction in LEDs. The depletion width of the p-side can be calculated from $$D = \sqrt{\frac{2\varepsilon V_{bi} N_D}{q N_A (N_A + N_D)}} \quad (8)$$

where $\varepsilon$ is the dielectric constant, $N_D$ is the carrier concentration of the n-GaN layer, $N_A$ is the carrier concentration of the p-GaN layer, and $V_{bi}$ is the built-in voltage $$V_{bi} = \frac{kT}{q} \ln \frac{N_A N_D}{n_i^2} \quad (9)$$

where n is the intrinsic carrier concentration. If $N_A$ and $N_D$ is $8 \times 10^{17}$ cm$^{-3}$ and $5 \times 10^{18}$ cm$^{-3}$, respectively, D is estimated to be 32 nm.

Based on the estimation method discussed above, the thickness of the p-GaN layer in a single Ag layer enhanced GaN 460 nm LED should be in the range of approximately 32 nm to 42 nm. The same principle can also be applied in the meta-material-LEDs. However, in the case of meta-material, d can possibly be made much larger by designing specific meta-material properties in accordance with the teachings provided herein. In addition, a longer operation wavelength also increases the value of d.

Two Dimensional Brownian motion imaging, for example for use with live cells, can be accomplished using one or more implementations of the current subject matter. This system could be either a physical system comprises only metallic or fluorescent particles in a liquid, or biological system such as fluorescence labeled signaling membrane proteins moving along a live cell membrane. Because the Z-resolution of MMEW microscopy can be compared to the size of the cell membrane and its associated protein complex (e.g. about 20 nm), MMEW microscopy can be capable of tracking the movement of surface membrane proteins between the inner and external surface of cell membranes (e.g. at about 5 nm in scale), which is not possible using conventional TIRF microscopy. MMEW microscopy can also be used for both scattering and fluorescent imaging.

Long-term fluorescence movies of cultured cells may also be possible using implemetations of the current subject matter since the cells are exposed to SP excited light only at their cell-substrate contact regions but not through their bulk and therefore tend to survive longer under observation, thereby enabling time-lapse recording of a week in duration. During this time, newly appearing cell-surface receptors can be immediately marked by fluorescent ligand that is continually present in the full cell culture medium. By utilizing MMEW microscopy, background fluorescence from this bath of unbound fluorophore can be minimized. Because of the super Z-resolution, significantly longer-term tracking can be enabled.

FIG. 25 shows a process flow chart illustrating features consistent with at least an implementation of the current subject matter. At 2502, surface plasmons are generated at an evanescent wave surface of a plasmonic condenser. The evanescent wave surface includes a metal layer such as is described herein as part of the plasmonic condenser. The plasmonic condenser also includes a substrate layer and a media layer disposed between the metal layer and the substrate layer. The media layer includes a source of radiation or light such as is described herein. The radiation from the source of radiation interacts with the metal layer to create the surface plasmons that are not substantially optically detectable as far field radiation. An interfering object is brought into proximity with the evanescent wave surface at 2504 and at least some of the surface plasmons at the evanescent wave surface are coupled at 2506 into propagating radiation detectable by an objective lens. The coupling includes the surface plasmons interacting with the interfering object. Optionally, at 2510, a decay distance of the propagating radiation is caused to be reduced relative to an original decay distance characteristic of the plasmonic condenser. This reducing can be accomplished at least in part by including in association with the plasmonic condenser a plasmonic meta-materials illuminator that includes a plurality of layers of meta-materials overlaying the metal layer.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed:

1. An apparatus comprising:
    a plasmonic condenser for generating surface plasmon at an evanescent wave surface, the plasmonic condenser comprising:
        a substrate layer;
        a metal layer comprising the evanescent wave surface; and
        a media layer disposed between the metal layer and the substrate layer, the media layer comprising a source of radiation, the radiation interacting with the metal layer to create surface plasmons that are not substantially optically detectable as far field radiation until an interfering object is brought into proximity with the evanescent wave surface, the interfering object causing coupling of at least some of the surface plasmons into propagating radiation detectable by an objective lens, the media layer further comprising at least one of a light emitting diode or an organic light emitting diode that emits the radiation at one or more wavelengths upon experiencing an applied voltage, the radiation being directly coupled into the surface plasmons.

2. An apparatus as in claim 1, further comprising the objective lens.

3. An apparatus as in claim 1, wherein the metal layer has sufficient thickness to serve as an attenuator to prevent directional transmission of the radiation from the source through the metal layer.

4. An apparatus as in claim 1, wherein the metal layer has a thickness in a range of approximately 10 nm to 150 nm.

5. An apparatus as in claim 1, wherein the metal layer has a thickness in a range of approximately 50 nm to 150 nm.

6. An apparatus as in claim 1, wherein the media layer comprises a fluorescent dye that emits the radiation at one or more transition wavelengths upon being excited by incident light provided via the substrate.

7. An apparatus as in claim 1, wherein the media layer comprises a coupling grating disposed beneath the metal layer, the coupling grating having a grating period that results in at least partial conversion of the radiation at one or more wavelengths into the surface plasmons upon being struck by incident light provided via the substrate.

8. An apparatus as in claim 1, wherein the metal layer serves as an electrode via which the applied voltage is delivered.

9. An apparatus as in claim 1, further comprising a plasmonic meta-materials illuminator that comprises the plasmonic condenser, the plasmonic meta-materials illuminator further comprising a plurality of layers of meta-materials overlaying the metal layer, the plurality of layers of meta-materials causing a decay distance of the propagating radiation to be reduced relative to an original decay distance characteristic of the plasmonic condenser.

10. A method comprising:
    generating surface plasmons at an evanescent wave surface of a plasmonic condenser, the evanescent wave surface comprising a metal layer, the plasmonic condenser comprising the metal layer, a substrate layer, and a media layer disposed between the metal layer and the substrate layer, the media layer comprising a source of radiation, the radiation interacting with the metal layer to create the surface plasmons that are not substantially optically detectable as far field radiation;
    bringing an interfering object into proximity with the evanescent wave surface; and
    coupling at least some of the surface plasmons at the evanescent wave surface into propagating radiation detectable by an objective lens, the coupling comprising the surface plasmons interacting with the interfering object, the media layer further comprising at least one of a light emitting diode or an organic light emitting diode that emits the radiation at one or more wavelengths upon experiencing an applied voltage, the radiation being directly coupled into the surface plasmons.

11. A method as in claim 10, further comprising detecting the propagating radiation with the objective lens.

12. A method as in claim 10, wherein the metal layer has sufficient thickness to serve as an attenuator to prevent directional transmission of the radiation from the source through the metal layer.

13. A method as in claim 10, wherein the metal layer has a thickness in a range of approximately 10 nm to 150 nm.

14. A method as in claim 10, wherein the metal layer has a thickness in a range of approximately 50 nm to 150 nm.

15. A method as in claim 10, wherein the media layer comprises a fluorescent dye that emits the radiation at one or more transition wavelengths upon being excited by incident light provided via the substrate.

16. A method as in claim 10, wherein the media layer comprises a coupling grating disposed beneath the metal layer, the coupling grating having a grating period that results in at least partial conversion of the radiation at one or more wavelengths into the surface plasmons upon being struck by incident light provided via the substrate.

17. A method as in claim 10, wherein the metal layer serves as an electrode via which the applied voltage is delivered.

18. A method as in claim 10, further comprising causing a decay distance of the propagating radiation to be reduced relative to an original decay distance characteristic of the plasmonic condenser, the causing comprising including, in association with the plasmonic condenser, a plasmonic meta-materials illuminator further comprising a plurality of layers of meta-materials overlaying the metal layer.

\* \* \* \* \*